US009867987B2

United States Patent
Ternes et al.

(10) Patent No.: US 9,867,987 B2
(45) Date of Patent: *Jan. 16, 2018

(54) REMOTE DETECTION OF PHYSIOLOGICAL PARAMETER USING AN IMPLANTABLE MEDICAL DEVICE

(71) Applicant: Cardiac Pacemakers, Inc., St. Paul, MN (US)

(72) Inventors: David J. Ternes, Roseville, MN (US); Kenneth L. Baker, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/196,579

(22) Filed: Jun. 29, 2016

(65) Prior Publication Data

US 2016/0303377 A1   Oct. 20, 2016

Related U.S. Application Data

(63) Continuation of application No. 14/590,480, filed on Jan. 6, 2015, now Pat. No. 9,381,358, which is a
(Continued)

(51) Int. Cl.
*A61N 1/00* (2006.01)
*A61N 1/36* (2006.01)
(Continued)

(52) U.S. Cl.
CPC .......... *A61N 1/36139* (2013.01); *A61B 5/024* (2013.01); *A61N 1/3605* (2013.01);
(Continued)

(58) Field of Classification Search
CPC .. A61N 1/36114; A61N 1/3605; A61B 5/024; A61B 5/0031; A61B 5/02055; A61B 5/02405; A61B 1/3605
See application file for complete search history.

(56) References Cited

U.S. PATENT DOCUMENTS 4,763,646 A   8/1988   Lekholm
5,058,600 A   10/1991  Schechter et al.
(Continued)

FOREIGN PATENT DOCUMENTS

AU   2009269901 A1   1/2010
AU   2010273544 B2   1/2011
(Continued)

OTHER PUBLICATIONS

"U.S. Appl. No. 12/835,308, Non Final Office Action dated Jan. 27, 2012", 9 pgs.
(Continued)

*Primary Examiner* — Robert N Wieland
(74) *Attorney, Agent, or Firm* — Schwegman Lundberg & Woessner, P.A.

(57) ABSTRACT

A system embodiment comprises a neural stimulator having a housing with an electrode on the housing and having a neural stimulation lead with an electrode on the neural stimulation lead. The neural stimulator is configured to deliver a neural stimulation therapy through the neural stimulation lead and remotely sense a heart rate using the electrode on the neural stimulation lead and the electrode on the housing of the neural stimulator.

20 Claims, 17 Drawing Sheets

Related U.S. Application Data continuation of application No. 14/249,632, filed on Apr. 10, 2014, now Pat. No. 8,942,799, which is a continuation of application No. 13/967,919, filed on Aug. 15, 2013, now Pat. No. 8,700,146, which is a continuation of application No. 13/627,551, filed on Sep. 26, 2012, now Pat. No. 8,515,534, which is a continuation of application No. 12/835,308, filed on Jul. 13, 2010, now Pat. No. 8,301,241.

(60) Provisional application No. 61/225,829, filed on Jul. 15, 2009.

(51) Int. Cl.
    *A61B 5/024*     (2006.01)
    *G06F 19/00*     (2011.01)
    *A61N 1/372*     (2006.01)

(52) U.S. Cl.
    CPC ...... *A61N 1/36053* (2013.01); *A61N 1/36114* (2013.01); *A61N 1/36146* (2013.01); *A61N 1/37211* (2013.01); *A61N 1/37288* (2013.01); *G06F 19/3406* (2013.01); *G06F 19/3418* (2013.01); *G06F 19/3481* (2013.01)

(56) References Cited

U.S. PATENT DOCUMENTS

| | | |
|---|---|---|
| 5,203,306 A | 4/1993 | Billingsley et al. |
| 5,203,326 A | 4/1993 | Collins |
| 5,628,777 A | 5/1997 | Moberg et al. |
| 5,687,738 A | 11/1997 | Shapiro et al. |
| 5,928,272 A | 7/1999 | Adkins et al. |
| 6,064,910 A | 5/2000 | Andersson et al. |
| 6,477,404 B1 | 11/2002 | Yonce et al. |
| 6,477,406 B1 | 11/2002 | Turcott |
| 7,123,961 B1 | 10/2006 | Kroll et al. |
| 7,127,290 B2 | 10/2006 | Girouard et al. |
| 7,162,304 B1 | 1/2007 | Bradley |
| 7,299,086 B2 | 11/2007 | McCabe et al. |
| 7,333,854 B1 | 2/2008 | Brewer et al. |
| 7,431,699 B2 | 10/2008 | Siejko et al. |
| 7,559,903 B2 | 7/2009 | Moussavi et al. |
| 7,689,276 B2 | 3/2010 | Dobak |
| 7,689,286 B2 | 3/2010 | Pastore et al. |
| 7,925,342 B2 | 4/2011 | Amurthur et al. |
| 7,951,087 B2 | 5/2011 | Siejko et al. |
| 7,974,696 B1 | 7/2011 | Dilorenzo |
| 8,285,373 B2 | 10/2012 | Ternes et al. |
| 8,301,241 B2 | 10/2012 | Ternes et al. |
| 8,515,534 B2 | 8/2013 | Ternes et al. |
| 8,571,654 B2 | 10/2013 | Libbus et al. |
| 8,577,458 B1 | 11/2013 | Libbus et al. |
| 8,588,906 B2 | 11/2013 | Ternes et al. |
| 8,594,805 B2 | 11/2013 | Hincapie Ordonez et al. |
| 8,626,281 B2 | 1/2014 | Ternes et al. |
| 8,626,292 B2 | 1/2014 | Mccabe et al. |
| 8,700,146 B2 | 4/2014 | Ternes et al. |
| 8,862,226 B2 | 10/2014 | Ternes et al. |
| 8,934,970 B2 | 1/2015 | Ternes et al. |
| 8,942,799 B2 | 1/2015 | Ternes et al. |
| 9,381,358 B2 | 7/2016 | Ternes et al. |
| 2004/0210261 A1 | 10/2004 | King et al. |
| 2005/0065575 A1 | 3/2005 | Dobak |
| 2005/0085866 A1 | 4/2005 | Tehrani |
| 2005/0107838 A1 | 5/2005 | Lovett et al. |
| 2005/0115561 A1 | 6/2005 | Stahmann et al. |
| 2005/0187586 A1 | 8/2005 | David et al. |
| 2006/0095081 A1 | 5/2006 | Zhou et al. |
| 2006/0195039 A1 | 8/2006 | Drew et al. |
| 2006/0206159 A1 | 9/2006 | Moffitt et al. |
| 2006/0271108 A1 | 11/2006 | Libbus et al. |
| 2007/0260285 A1 | 11/2007 | Libbus et al. |
| 2008/0021504 A1 | 1/2008 | McCabe et al. |
| 2008/0051839 A1 | 2/2008 | Libbus et al. |
| 2008/0058871 A1 | 3/2008 | Libbus et al. |
| 2008/0058872 A1 | 3/2008 | Brockway et al. |
| 2008/0058874 A1 | 3/2008 | Westlund et al. |
| 2008/0071327 A1 | 3/2008 | Miesel et al. |
| 2008/0086181 A1 | 4/2008 | Amurthur et al. |
| 2008/0147140 A1 | 6/2008 | Ternes et al. |
| 2008/0161894 A1 | 7/2008 | Ben-David et al. |
| 2008/0177191 A1 | 7/2008 | Patangay et al. |
| 2008/0234780 A1 | 9/2008 | Smith et al. |
| 2008/0243017 A1 | 10/2008 | Moussavi et al. |
| 2008/0243196 A1 | 10/2008 | Libbus et al. |
| 2008/0269842 A1* | 10/2008 | Giftakis ............ A61N 1/36082 607/62 |
| 2008/0294208 A1 | 11/2008 | Willis et al. |
| 2009/0030292 A1 | 1/2009 | Bartnik et al. |
| 2009/0292217 A1 | 11/2009 | Bartnik et al. |
| 2010/0010556 A1 | 1/2010 | Zhao et al. |
| 2010/0249627 A1 | 9/2010 | Zhang et al. |
| 2010/0305647 A1 | 12/2010 | Mccabe et al. |
| 2011/0015702 A1 | 1/2011 | Ternes et al. |
| 2011/0015703 A1 | 1/2011 | Ternes et al. |
| 2011/0015704 A1 | 1/2011 | Ternes et al. |
| 2011/0282416 A1 | 11/2011 | Hamann et al. |
| 2011/0313488 A1 | 12/2011 | Ordonez et al. |
| 2012/0095530 A1 | 4/2012 | Chavan et al. |
| 2012/0143286 A1 | 6/2012 | Hahn et al. |
| 2012/0271382 A1 | 10/2012 | Arcot-Krishnamurthy et al. |
| 2012/0316622 A1 | 12/2012 | Whitehurst et al. |
| 2013/0023956 A1 | 1/2013 | Ternes et al. |
| 2013/0023957 A1 | 1/2013 | Ternes et al. |
| 2013/0158616 A1 | 6/2013 | Libbus et al. |
| 2013/0158618 A1 | 6/2013 | Libbus et al. |
| 2013/0158622 A1 | 6/2013 | Libbus et al. |
| 2013/0238047 A1 | 9/2013 | Libbus et al. |
| 2013/0289646 A1 | 10/2013 | Libbus et al. |
| 2013/0331904 A1 | 12/2013 | Ternes et al. |
| 2014/0052209 A1 | 2/2014 | Ternes et al. |
| 2014/0094875 A1 | 4/2014 | Ternes et al. |
| 2014/0222115 A1 | 8/2014 | Ternes et al. |
| 2015/0127067 A1 | 5/2015 | Ternes et al. |

FOREIGN PATENT DOCUMENTS

| | | |
|---|---|---|
| AU | 2010273546 B2 | 12/2013 |
| CN | 102481453 A | 5/2012 |
| EP | 0253505 A2 | 1/1988 |
| EP | 2453975 B1 | 11/2016 |
| JP | 2008541850 A | 11/2008 |
| JP | 2012533349 A | 12/2012 |
| JP | 2012533350 A | 12/2012 |
| JP | 2012533351 A | 12/2012 |
| JP | 5624619 B2 | 10/2014 |
| WO | WO-9519201 A1 | 7/1995 |
| WO | WO-2006069215 A2 | 6/2006 |
| WO | WO-2007027940 A2 | 3/2007 |
| WO | WO-2008024557 A1 | 2/2008 |
| WO | WO-2008115507 A1 | 9/2008 |
| WO | WO-2010005482 A1 | 1/2010 |
| WO | WO-2011008747 A2 | 1/2011 |
| WO | WO-2011008748 A2 | 1/2011 |
| WO | WO-2011008748 A3 | 1/2011 |
| WO | WO-2011008749 A2 | 1/2011 |
| WO | WO-2011008747 A3 | 3/2011 |
| WO | WO-2011008749 A3 | 3/2011 |

OTHER PUBLICATIONS

"U.S. Appl. No. 12/835,308, Notice of Allowance dated Jun. 26, 2012", 9 pgs.

"U.S. Appl. No. 12/835,308, Response filed Apr. 26, 2012 to Non Final Office Action dated Jan. 27, 2012", 11 pgs.

"U.S. Appl. No. 13/627,551, Notice of Allowance dated Apr. 25, 2013", 10 pgs.

"U.S. Appl. No. 13/967,919, Notice of Allowance dated Nov. 29, 2013", 14 pgs.

"U.S. Appl. No. 14/249,632, Notice of Allowance dated Sep. 17, 2014", 10 pgs.

(56) References Cited

OTHER PUBLICATIONS

"U.S. Appl. No. 14/249,632, Preliminary Amendment filed Apr. 14, 2014", 5 pgs.
"U.S. Appl. No. 14/590,480, Non Final Office Action dated Jun. 22, 2015", 15 pgs.
"U.S. Appl. No. 14/590,480, Non Final Office Action dated Oct. 15, 2015", 10 pgs.
"U.S. Appl. No. 14/590,480, Notice of Allowance dated Mar. 2, 2016", 8 pgs.
"U.S. Appl. No. 14/590,480, Preliminary Amendment filed Jan. 7, 2015", 6 pgs.
"U.S. Appl. No. 14/590,480, Response filed Sep. 22, 2015 to Non Final Office Action dated Jun. 22, 2015", 10 pgs.
"International Application Serial No. PCT/US2010/041816, International Preliminary Report on Patentability dated Jan. 26, 2012", 11 pgs.
"International Application Serial No. PCT/US2010/041816, International Search Report dated Oct. 7, 2011", 6 pgs.
"International Application Serial No. PCT/US2010/041816, Invitation to Pay Additional Fee dated Apr. 26, 2011", 7 pgs.
"International Application Serial No. PCT/US2010/041816, Written Opinion dated Oct. 7, 2011", 10 pgs.
Gavriely, N, "Spectral characteristics of normal breath sounds", J Appl Physiol., 50(2), (Feb. 1981), 307-14.
Gavriely, N., et al., "Spectral characteristics of chest wall breath sounds in normal subjects.", Thorax, 50(12), (Dec. 1995), 1292-300.
Yadollahi, A., et al., "A robust method for estimating respiratory flow using tracheal sounds entropy", IEEE Transactions on Biomedical Engineering, 53(4), (2006), 662-668.
Yadollahi, A., et al., "Acoustical Respiratory Flow", IEEE Engineering in Medicine and Biology Magazine, 26(1), (2007), 56-61.
Yadollahi, A., et al., "Apnea Detection by Acoustical Means", 28th Annual International Conference of the IEEE Engineering in Medicine and Biology Society, 2006. EMBS '06., (2006), 4623-4626.
Yeh, Y. C, et al., "QRS complexes detection for ECG signal: the Difference Operation Method.", Comput Methods Programs Biomed., 91(3), (Sep. 2008), 245-54.
"Japanese Application Serial No. 2012-520716, Examiners Decision of Final Refusal dated Dec. 26, 2013", With English Translation, 4 pgs.
"Japanese Application Serial No. 2012-520716, Office Action dated May 29, 2013", With English Translation, 5 pgs.
"European Application Serial No. 10735379.9, Communication Pursuant to Article 94(3) EPC dated Jul. 25, 2017", 9 pgs.

* cited by examiner

REMOTE DETECTION OF PHYSIOLOGICAL PARAMETER USING AN IMPLANTABLE MEDICAL DEVICE

CLAIM OF PRIORITY

This application is a continuation of and claims the benefit of priority under 35 U.S.C. §120 to U.S. patent application Ser. No. 14/590,480, filed on Jan. 6, 2015, now issued as U.S. Pat. No. 9,381,358, which is a continuation of and claims the benefit of priority under 35 U.S.C. §120 to U.S. patent application Ser. No. 14/249,632, filed on Apr. 10, 2014, now issued as U.S. Pat. No. 8,942,799, which is a continuation of and claims the benefit of priority under 35 U.S.C. §120 to U.S. patent application Ser. No. 13/967,919, filed on Aug. 15, 2013, now issued as U.S. Pat. No. 8,700,146, which is a continuation of and claims the benefit of priority under 35 U.S.C. §120 to U.S. patent application Ser. No. 13/627,551, filed on Sep. 26, 2012, now issued as U.S. Pat. No. 8,515,534, which is a continuation of and claims the benefit of priority under 35 U.S.C. §120 to U.S. patent application Ser. No. 12/835,308, filed on Jul. 13, 2010, now issued as U.S. Pat. No. 8,301,241, which claims the benefit of priority under 35 U.S.C. §119(e) of U.S. Provisional Patent Application Ser. No. 61/225,829, filed on Jul. 15, 2009, the benefit of priority of each of which is claimed hereby, and each of which are incorporated by reference herein in its entirety.

TECHNICAL FIELD

This application relates generally to medical devices and, more particularly, to systems, devices and methods for remotely sensing paced cardiac activity.

BACKGROUND

Implanting a chronic electrical stimulator, such as a cardiac stimulator, to deliver medical therapy(ies) is known. Examples of cardiac stimulators include implantable cardiac rhythm management (CRM) devices such as pacemakers, implantable cardiac defibrillators (ICDs), and implantable devices capable of performing pacing and defibrillating functions.

CRM devices are implantable devices that provide electrical stimulation to selected chambers of the heart in order to treat disorders of cardiac rhythm. An implantable pacemaker, for example, is a CRM device that paces the heart with timed pacing pulses. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output.

It has been proposed to stimulate neural targets (referred to as neural stimulation, neurostimulation or neuromodulation) to treat a variety of pathological conditions. For example, research has indicated that electrical stimulation of the carotid sinus nerve can result in reduction of experimental hypertension, and that direct electrical stimulation to the pressoreceptive regions of the carotid sinus itself brings about reflex reduction in experimental hypertension.

SUMMARY

Various embodiments discussed herein relate to the remote sensing of paced cardiac activity.

A system embodiment for stimulating a neural target comprises a neural stimulator, a pace detector, and a controller. The neural stimulator is electrically connected to at least one electrode, and is configured to deliver a neural stimulation signal through the at least one electrode to stimulate the neural target. The pace detector is configured to use at least one electrode to sense cardiac activity and distinguish paced cardiac activity in the sensed cardiac activity from non-paced cardiac activity in the sensed cardiac activity. The controller is configured to control a programmed neural stimulation therapy using the neural stimulator and using detected paced cardiac activity as an input for the neural stimulation therapy.

According to an embodiment of method for operating an implanted neural stimulation device, a pace detector in the implanted neural stimulation device is used to sense cardiac activity and distinguish between paced cardiac activity and non-paced cardiac activity. A programmed neural stimulation therapy performed by the implanted neural stimulation device is controlled using detected cardiac activity as an input for the neural stimulation therapy.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
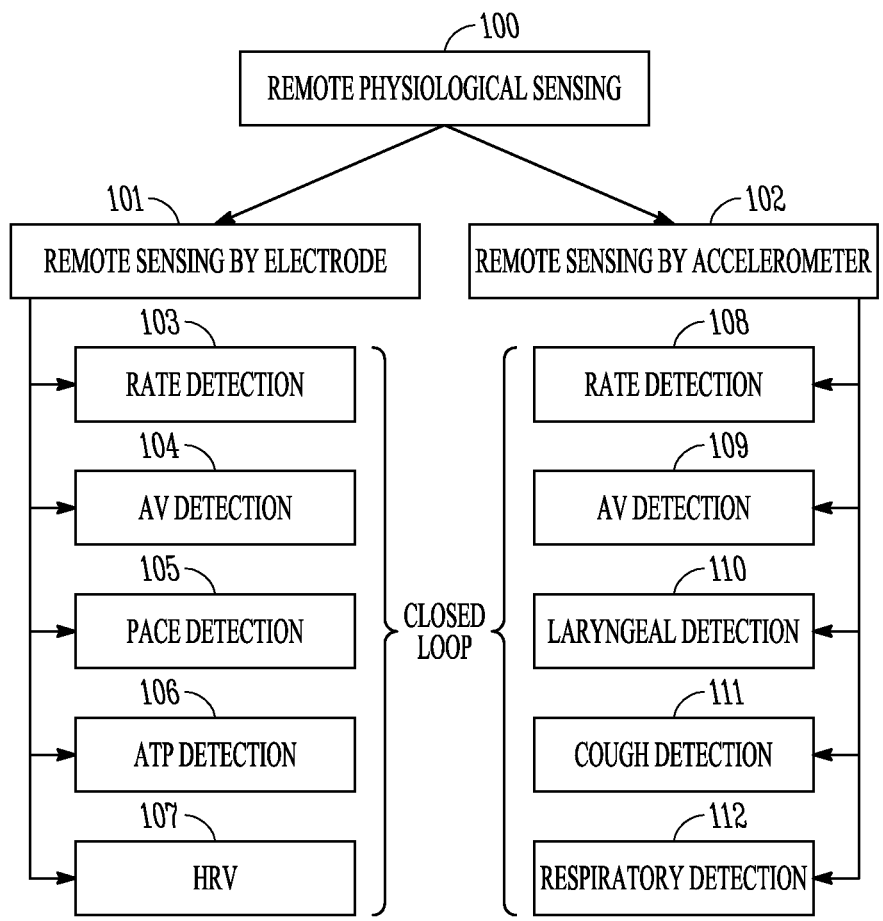
FIG. 1 illustrates various technologies for sensing physiologic signals used in various embodiments of the present subject matter.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Physiology Overview

Provided herein, for the benefit of the reader, is a brief discussion of physiology related to autonomic neural stimulation. The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The heart rate and force are increased when the sympathetic nervous system is stimulated, and is decreased when the sympathetic nervous system is inhibited (or the parasympathetic nervous system is stimulated). An afferent nerve conveys impulses toward a nerve center. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intention, increases urine secretion, and contracts the wall and relaxes the sphincter of the bladder. The functions associated with the sympathetic and parasympathetic nervous systems are many and can be complexly integrated with each other.

Vagal modulation may be used to treat a variety of cardiovascular disorders, including but not limited to heart failure, post-MI (myocardial infarction) remodeling, and hypertension. These conditions are briefly described below.

Heart failure refers to a clinical syndrome in which cardiac function causes a below normal cardiac output that can fall below a level adequate to meet the metabolic demand of tissues. Heart failure may present itself as congestive heart failure (CHF) due to the accompanying venous and pulmonary congestion. Heart failure can be due to a variety of etiologies such as ischemic heart disease, hypertension and diabetes.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

Cardiac remodeling refers to a complex remodeling process of the ventricles that involves structural, biochemical, neurohormonal, and electrophysiologic factors, which can result following an MI or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamics, sympathetic nervous system and hormonal alterations (such as presence or absence of angiotensin converting enzyme (ACE) activity) accounts for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Therapy Examples

Various embodiments provide a stand-alone device, either externally or internally, to provide neural stimulation therapy. For example, the present subject matter may deliver anti-remodeling therapy through neural stimulation as part of a post-MI or heart failure therapy. Neural stimulation may also be used in a hypertension therapy and conditioning therapy, by way of example and not limitation. The present subject matter may also be implemented in non-cardiac applications, such as in therapies to treat epilepsy, depression, pain, obesity, hypertension, sleep disorders, and neuropsychiatric disorders. Various embodiments provide systems or devices that integrate neural stimulation with one or more other therapies, such as bradycardia pacing, anti-tachycardia therapy, remodeling therapy, and the like.

Neural Stimulation Therapies

Examples of neural stimulation therapies include neural stimulation therapies for respiratory problems such a sleep disordered breathing, for blood pressure control such as to treat hypertension, for cardiac rhythm management, for myocardial infarction and ischemia, for heart failure, for epilepsy, for depression, for pain, for migraines and for eating disorders and obesity. Many proposed neural stimulation therapies include stimulation of the vagus nerve. This listing of other neural stimulation therapies is not intended to be an exhaustive listing. Neural stimulation can be provided using electrical, acoustic, ultrasound, light, and magnetic stimulation. Electrical neural stimulation can be delivered using any of a nerve cuff, intravascularly-fed lead, or transcutaneous electrodes.

A therapy embodiment involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electrostimulatory means to modulate autonomic activity, referred to as anti-remodeling therapy (ART). When delivered in conjunction with ventricular resynchronization pacing, also referred to as remodeling control therapy (RCT), such modulation of autonomic activity may act synergistically to reverse or prevent cardiac remodeling.

One neural stimulation therapy embodiment involves treating hypertension by stimulating the baroreflex for sustained periods of time sufficient to reduce hypertension. The baroreflex is a reflex that can be triggered by stimulation of a baroreceptor or an afferent nerve trunk. Baroreflex neural targets include any sensor of pressure changes (e.g. sensory nerve endings that function as a baroreceptor) that is sensitive to stretching of the wall resulting from increased pressure from within, and that functions as the receptor of the central reflex mechanism that tends to reduce that pressure. Baroreflex neural targets also include neural pathways extending from the baroreceptors. Examples of nerve trunks that can serve as baroreflex neural targets include the vagus, aortic and carotid nerves.

Myocardial Stimulation Therapies

Various neural stimulation therapies can be integrated with various myocardial stimulation therapies. The integration of therapies may have a synergistic effect. Therapies can be synchronized with each other, and sensed data can be shared between the therapies. A myocardial stimulation therapy provides a cardiac therapy using electrical stimulation of the myocardium. Some examples of myocardial stimulation therapies are provided below.

A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. A CRT example applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur. Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected. ATP may be referred to as overdrive pacing. Other overdrive pacing therapies exist, such as intermittent pacing therapy (IPT), which may also be referred to as a conditioning therapy.

Remote Physiological Sensing

Various embodiments of implanted neuromodulation devices use physiological sensing to enhance therapies or diagnostics. For example, various embodiments provide a therapy based on rate, a therapy tied to a cardiac cycle, a therapy tied to antitachycardia pacing (ATP) detection, a therapy tied to an average heart rate, a therapy tied to heart rate variability (HRV), or a therapy tied to other cardiac diagnostics. Various embodiments provide input such as these to an implanted neuromodulation device without implanted cardiac leads.

Remote sensing of cardiac activity, cardiac pacing, laryngeal vibration, cough and/or other electromechanical physiological activity can provide input into neuromodulation titration algorithms, neuromodulation therapy driver algorithms, neuromodulation heart failure diagnostics and other diagnostics and features. FIG. 1 illustrates various technologies for sensing physiologic signals used in various embodiments of the present subject matter. For example, remote physiological sensing 100, such as may be used to provide a closed loop therapy or provide diagnostics, may be performed using an electrode or may be performed using an accelerometer (XL) 102. An electrode used to remotely sense cardiac activity can be used to detect heart rate 103, to detect an AV interval 104, to detect paces provided by a cardiac rhythm management (CRM) device 105, to detect antitachycardia pacing (ATP) 106, or to measure heart rate variability (HRV) 107. These examples are not intended to be an exclusive listing, as remotely sensed cardiac activity can be used in a variety of algorithms. An accelerometer may be used to remotely sense cardiac activity, and thus may be used to detect heart rate 108 or to detect an AV interval 109. An accelerometer may also be used to detect laryngeal vibrations 110, cough 111 or respiratory activity 112, which can serve as feedback or other input for a neural stimulation therapy such as a vagus nerve stimulation therapy.

Figure 2:
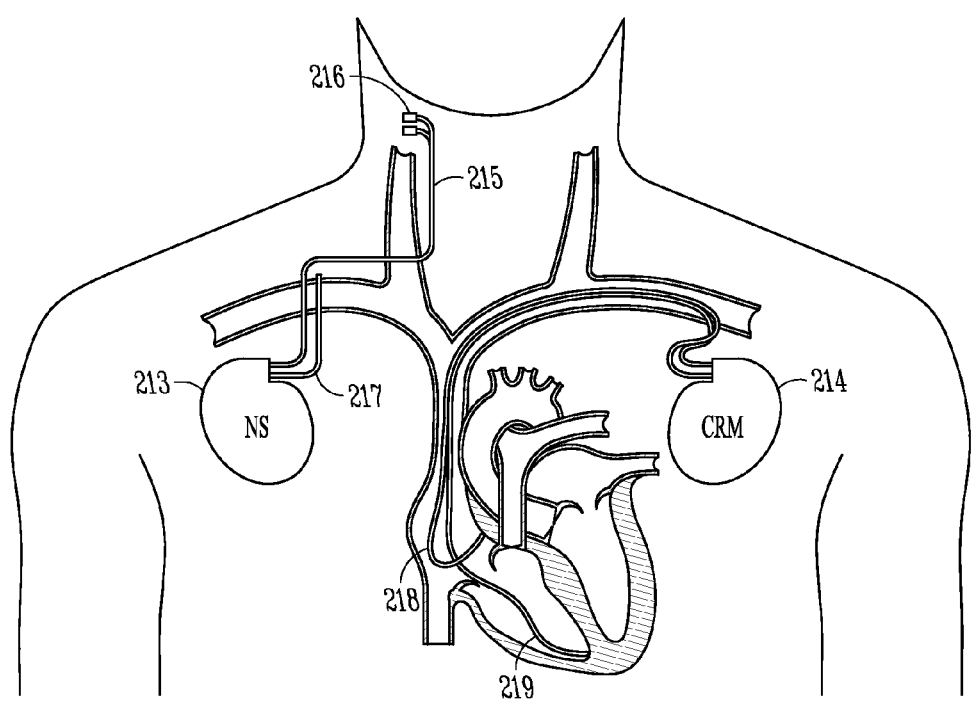
FIG. 2 illustrates an implantable neural stimulator and an implantable CRM device, according to various embodiments.

FIG. 2 illustrates an implantable neural stimulator 213 and an implantable CRM device 214, according to various embodiments. For example, the neural stimulator 213 may be configured to stimulate a vagus nerve in the cervical region, as illustrated in the figure. Examples of CRM devices include pacemakers, anti-arrhythmia devices such as defibrillators and anti-tachycardia devices, and devices to deliver cardiac resynchronization therapy (CRT). The illustrated neural stimulator 213 has a neural stimulation lead 215 for use to deliver neural stimulation. The illustrated lead embodiment has a nerve cuff electrode 216. Other lead embodiments provide transvascular stimulation of the nerve (e.g. stimulation of the vagus nerve from the internal jugular vein). In some embodiments, the neural stimulation lead 215 has neural sensing capabilities, and/or remote sensing capabilities (e.g. accelerometer and/or electrode sensing). Some embodiments of a neural stimulator 213 have a stub lead 217 to provide remote sensing capabilities. The illustrated CRM device 214 includes a right atrial lead 218 and a right ventricle lead 219. Other leads, additional leads, or fewer leads may be used for various device embodiments. In some embodiments, the neural stimulator 213 is a vagal nerve stimulator, such as generally illustrated in FIG. 2. In some embodiments, the neural stimulator is a spinal cord stimulator.

According to some embodiments, the neural stimulator device is the only implanted medical device in the patient. In some embodiments, the patient is implanted with both the neural stimulator device and the CRM device. Some embodiments provide communication between the neural stimulator and the CRM device. The communication may be wireless or may be through a wired connection such as a tether between the two devices. In some embodiment the neural stimulator operates without communicating with the CRM device, and thus independently senses paces, heart rate, and the like.

Various embodiments of the present subject matter use an accelerometer to remotely sense Heart Rate Variability (HRV) and perform Heart Failure (HF) diagnostics. HRV and other HF diagnostics may be based on the timing between R-waves. Some embodiments store the S1 interval data obtained from heart sounds and use this data for HRV diagnostics in lieu of R-wave intervals.

An accelerometer in an implanted medical device can be used to ascertain heart sounds. Known type heart sounds include the "first heart sound" or S1, the "second heart sound" or S2, the "third heart sound" or S3, the "fourth heart sound" or S4, and their various sub-components. Heart sounds can be used in determining a heart failure status. The first heart sound ($S_1$), is initiated at the onset of ventricular systole and consists of a series of vibrations of mixed, unrelated, low frequencies. $S_1$ is chiefly caused by oscillation of blood in the ventricular chambers and vibration of the chamber walls. The intensity of $S_1$ is primarily a function of the force of the ventricular contraction, but also of the interval between atrial and ventricular systoles. The second heart sound ($S_2$), which occurs on closure of the semi-lunar valves, is composed of higher frequency vibrations, is of shorter duration and lower intensity, and has a more "snapping" quality than the first heart sound. The second sound is caused by abrupt closure of the semi-lunar valves, which initiates oscillations of the columns of blood and the tensed vessel walls by the stretch and recoil of the closed valve. The third heart sound ($S_3$), which is more frequently heard in children with thin chest walls or in patients with rapid filling wave due to left ventricular failure, consists of a few low intensity, low-frequency vibrations. It occurs in early diastole and is believed to be due to vibrations of the ventricular walls caused by abrupt acceleration and deceleration of blood entering the ventricles on opening of the atrial ventricular valves. A fourth or atrial sound ($S_4$), consisting of a few low-frequency oscillations, is occasionally heard in normal individuals. It is caused by oscillation of blood and cardiac chambers created by atrial contraction. Accentuated $S_3$ and $S_4$ sounds may be indicative of certain abnormal conditions and are of diagnostic significance. For example, a more severe HF status tends to be reflected in a larger $S_3$ amplitude. The term "heart sound" hereinafter refers to any heart sound (e.g., S1) and any components thereof (e.g., M1 component of S1, indicative of Mitral valve closure). S1, S2 and maybe S3 sounds may be distinguished from the accelerometer signal. "Heart sounds" include audible mechanical vibrations caused by cardiac activity that can be sensed with a microphone and audible and inaudible mechanical vibrations caused by cardiac activity that can be sensed with an accelerometer.

Figure 3:
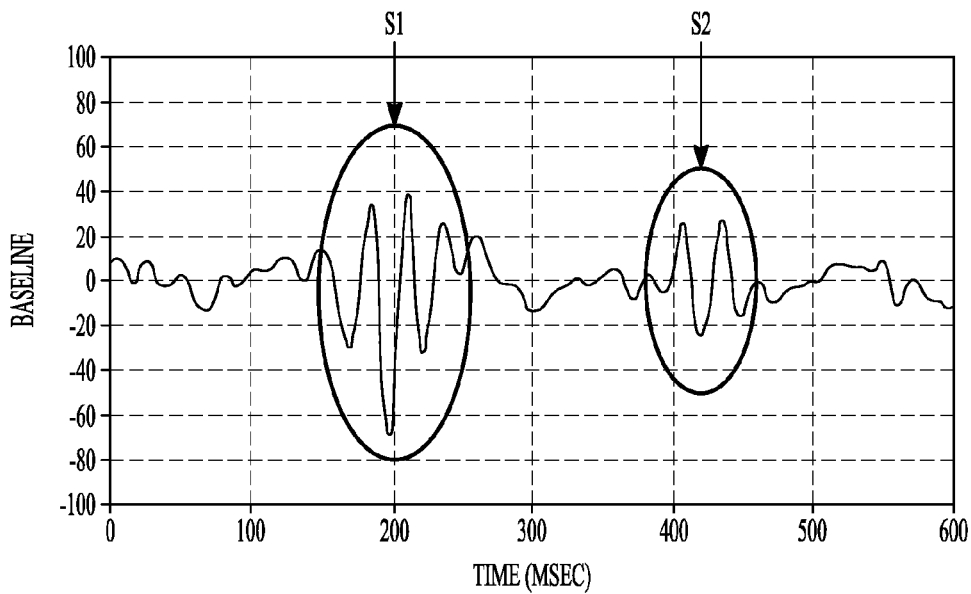
FIG. 3 illustrates heart sounds S1 and S2, such as may be detected using an accelerometer.
Figure 4:
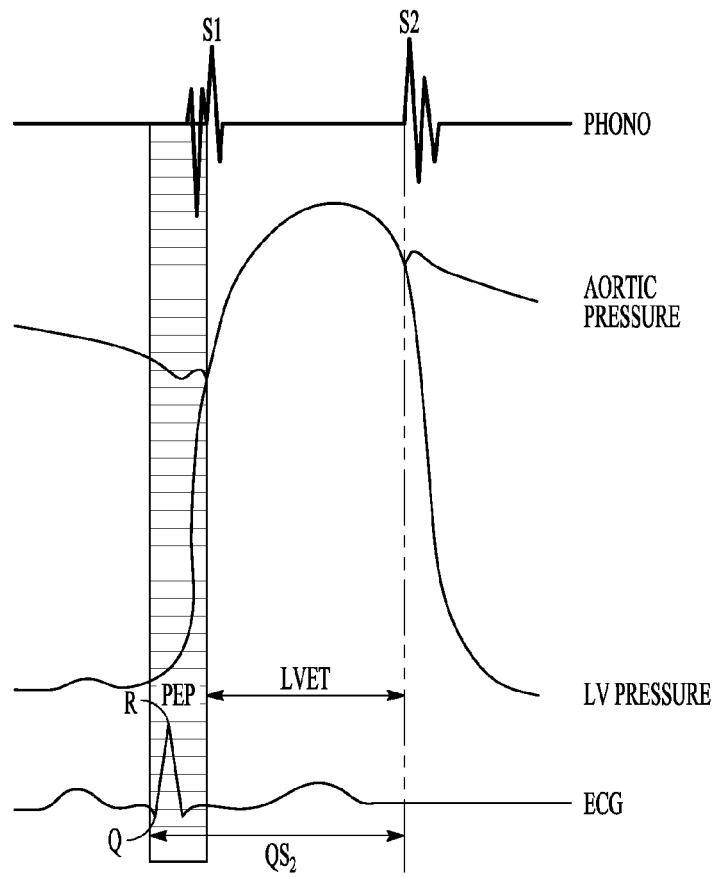
FIG. 4 illustrates a relationship between heart sounds and both the QRS wave and left ventricular pressure.

Patangay et al. (US 20080177191), now U.S. Pat. No. 7,736,319, which is incorporated herein by reference in its entirety, discuss heart sounds and a relationship between heart sounds and both QRS wave and left ventricular pressure. FIG. 3 illustrates heart sounds S1 and S2 such as may be detected using an accelerometer; and FIG. 4 illustrates a relationship between heart sounds and both the QRS wave and left ventricular pressure.

Figure 5:
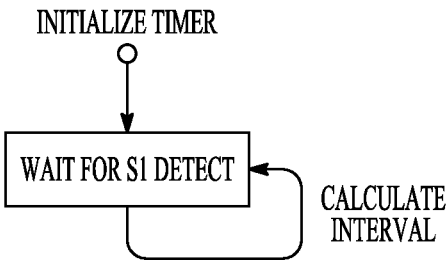
FIG. 5 illustrates an embodiment of a method for calculating an interval between heart sounds, used to determine heart rate.

A rate determination can be made by calculating the interval between S1 sounds or other heart sounds (e.g. S2 to S2, or S3 to S3 or S4 to S4. S1 is used as an example. FIG. 5 illustrates an embodiment of a method for calculating an interval between heart sounds, used to determine heart rate. A timer is initialized, and the method waits for a detected S1 sound. An interval is calculated between successive S1 sounds.

Figure 6:
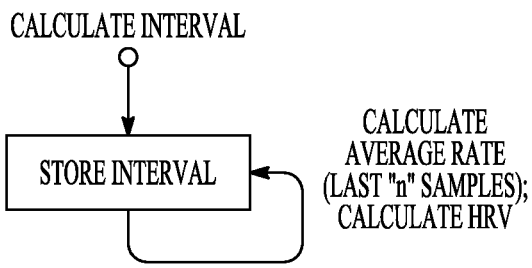
FIG. 6 illustrates an embodiment of a method for using heart sounds to calculate an average rate or to calculate HRV.

Average heart rate over a period of time can be determined once the S1 intervals are calculated. Various embodiments provide cardiac rate averages over discreet periods of time based on the S1 sound or the S2 heart sound. FIG. 6 illustrates an embodiment of a method for using heart sounds to calculate an average rate or to calculate HRV. Calculated intervals between heart sounds (e.g. S1 sounds) are stored. A plurality of sample intervals are stored, and are used to calculate an average heart rate over a number of samples. The plurality of sample intervals may be used to calculate a measure of heart rate variability.

Figure 7:
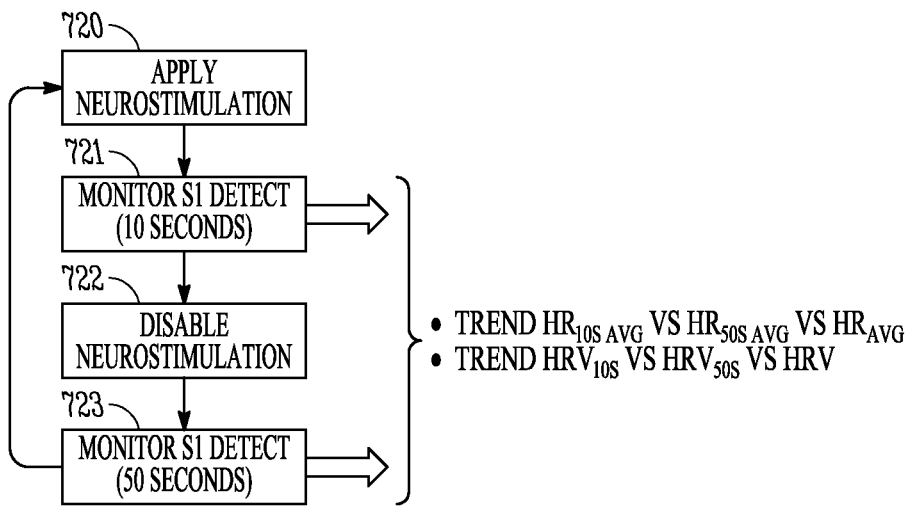
FIG. 7 illustrates an embodiment of a method for using heart sounds to determine heart rate during time periods with neural stimulation and time periods without neural stimulation.

A neural stimulation therapy may intermittently apply neural stimulation. Various embodiments trend the average heart rate for when the neural stimulation is ON and when the neural stimulation is OFF. FIG. 7 illustrates an embodiment of a method for using heart sounds to determine heart rate during time periods with neural stimulation and time periods without neural stimulation. For example, some embodiments apply neural stimulation with a duty cycle with an ON portion (e.g. a train of pulses for approximately 10 seconds for each minute) and an OFF portion (e.g. approximately 50 seconds). The present subject matter is not limited to embodiments with a 10 second ON portion and a 50 second OFF portion, as other timing for the ON portion and/or the OFF portion may be used. Thus, in the illustrated embodiment, neural stimulation is applied for about 10 seconds at 720. As represented at 721, the number of detected S1 sounds is identified during these ten seconds of applied neural stimulation. At 722, after the 10 seconds of neural stimulation, the neural stimulation is disabled for the OFF portion of the duty cycle (e.g. about 50 seconds). As represented at 723, the number of detected S1 sounds is identified during the period of disabled neural stimulation, before neural stimulation is again applied at 720. The overall heart rate (HR) can be calculated, as well as the heart rate during periods of applied neural stimulation ($HR_{10}$) and periods without neural stimulation ($HR_{50}$). Each of these heart rates can be averaged over various predetermined periods of time. For example, the overall heart rate (HR) may be averaged over each minute, over a fraction of the minute, or over multiple minutes. The heart rate during periods of applied neural stimulation ($HR_{10}$) may be averaged over the entire duration of a neural stimulation episode (e.g. 10 seconds), over a fraction of each neural stimulation episode, or over multiple neural stimulation episodes. The heart rate periods without neural stimulation ($HR_{50}$) may be averaged over the entire duration of an episode of disabled neural stimulation (e.g. 50 seconds), over a fraction of each episode of disabled neural stimulation, or over multiple episodes of disabled neural stimulation. Additionally, HRV may be determined over a period that includes both times with and without neural stimulation (HRV), over a period of time only when neural stimulation is applied ($HRV_{10}$), or over a period of time only when neural stimulation is not applied ($HRV_{50}$). The trending of heart rate, HRV, left ventricular ejection time (LVET) (S1 to S2), AV Delay, and the like can be performed using heart sounds or remote ECG analysis.

Figure 8:
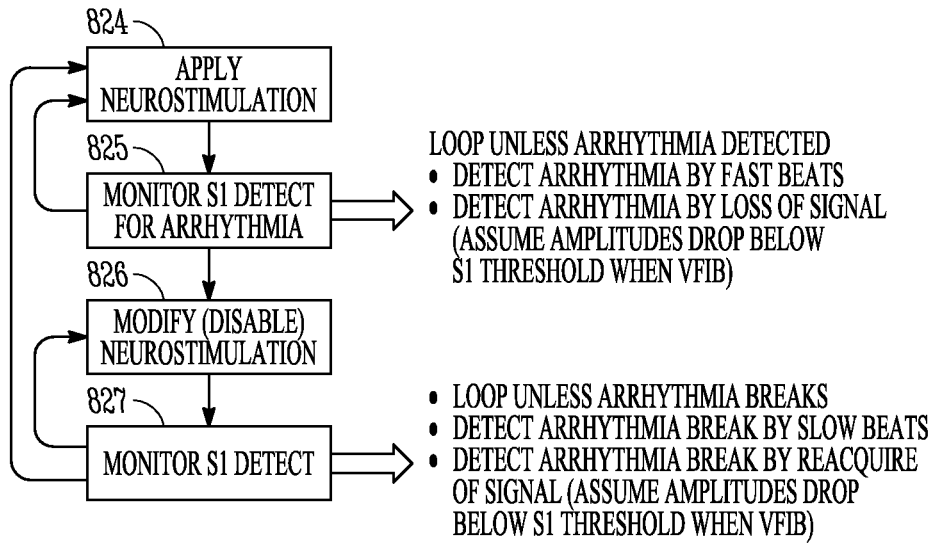
FIG. 8 illustrates an embodiment of a method for using heart sounds to detect arrhythmia.

According to various embodiments, a neural stimulation therapy is altered or suspended upon detection of an arrhythmia. Heart sound intervals (e.g. S1 intervals) can be used to remotely detect a ventricular arrhythmia. FIG. 8 illustrates an embodiment of a method for using heart sounds to detect arrhythmia. At 824, neural stimulation is applied for a period of time. During the period of time with neural stimulation, S1 sounds are monitored to detect for an arrhythmia, as represented at 825. An arrhythmia may be detected by fast beats or by a loss of signal caused by the amplitudes of the sound signal dropping below the S1 threshold during fibrillation. If no arrhythmia is detected, the illustrated method loops back to 824 to continue to apply neural stimulation. At 826, in response to a detected arrhythmia, the neural stimulation is modified or disabled. After modifying or disabling the neural stimulation, S1 sounds are monitored to determine if the arrhythmia breaks. If the arrhythmia continues, the illustrated method returns back to 824. An arrhythmia break may be detected by slow beats, or by reacquiring a signal caused by the sound signal amplitude rising above the S1 threshold after the arrhythmia breaks.

Figure 9:
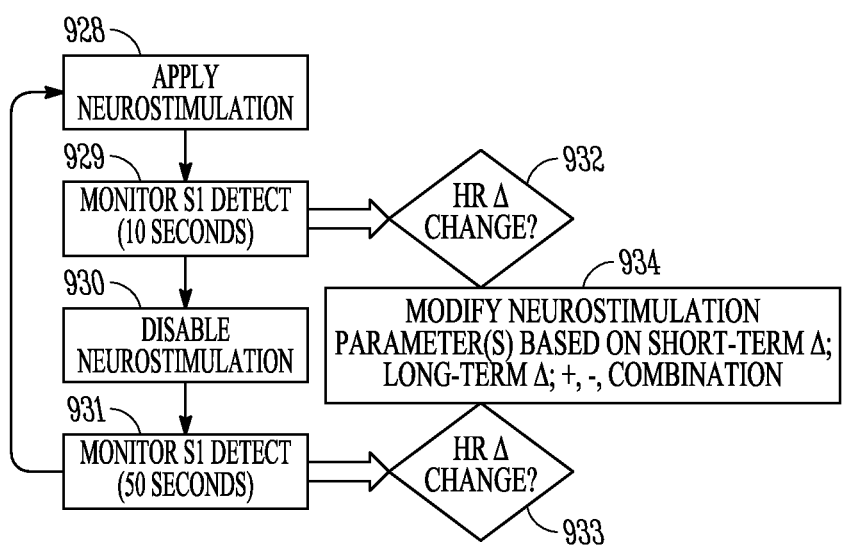
FIG. 9 illustrates an embodiment of a method for modulating neural stimulation based on heart rate determined using heart sounds.

FIG. 9 illustrates an embodiment of a method for modulating neural stimulation based on heart rate determined using heart sounds. For example, some embodiments apply neural stimulation for approximately 10 seconds for each minute. Thus, in the illustrated method, neural stimulation is applied for about 10 seconds at 928. As represented at 929, the number of detected S1 sounds is identified during these ten seconds of applied neural stimulation. At 930, after the 10 seconds of neural stimulation, the neural stimulation is disabled for about 50 seconds. As represented at 931, the number of detected S1 sounds is identified during the period of disabled neural stimulation, before neural stimulation is again applied at 928. At 932, a heart rate change is determined using the S1 sounds detected during the neural stimulation; and at 933, a heart rate change is determined using the S1 sounds detected during times without neural stimulation. These heart rate changes are used to modify the neural stimulation, as generally illustrated at 934. The modification to the neural stimulation may be based on short term heart rate changes, long term heart rate changes, or a combination of both short and long term heart rate changes. The modification of the neural stimulation can be based on response to physiological need (exercise, stress) or need to change dosing due to change in health status (lower HR due to better HF). By way of example, and not limitation, some embodiments deliver neural stimulation that does not significantly alter heart rate. The therapy intensity (e.g. amplitude of the stimulation signal) may be reduced if the neural stimulation is consistently associated with an undesired heart rate change; or if an acute change in heart rate occurred during the latter portion of the ON time, the duration of the ON time could be altered or the intensity of the therapy (e.g. amplitude of the stimulation signal) may be reduced during the latter portion of the ON time. In some embodiments, a determination of a long term change in heart rate (e.g. lower heart rate due to improvement in heart failure) causes the device to change to a maintenance dose mode of therapy (e.g. delivering therapy for only a couple of hours a day). Various embodiments monitor for a divergence between the chronic average heart rate during the ON period and the chronic average heart rate during the OFF period, or other unexpected things, that may require a different therapy response.

Figure 10:
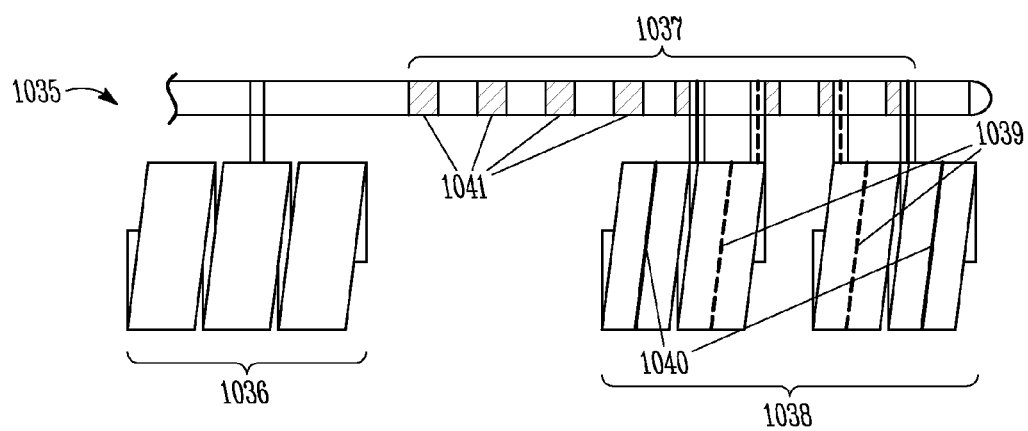
FIG. 10 illustrates an embodiment of a combined neural lead with dedicated neural stimulation electrodes and cardiac electrogram sensing electrodes (unipolar to can or bipolar).

Various embodiments of the present subject matter use an electrode to remotely sense cardiac activity. FIG. 10 illustrates an embodiment of a combined neural lead 1035 with dedicated neural stimulation electrodes and cardiac electrogram sensing electrodes (unipolar to can or bipolar). The illustrated lead includes a strain relief cuff 1036, and a plurality of electrodes 1037. The plurality of electrodes 1037 includes a neural electrode cuff 1038 that includes both neural therapy electrodes 1039 used to deliver neural stimulation and neural sensing electrodes 1040 used to detect action potentials in the nerve. The plurality of electrodes in the illustrated lead embodiment also includes cardiac ECG sensing electrodes 1041 (e.g. electrodes to remotely sense cardiac activity). The cardiac ECG sensing electrodes may either be bipolar electrodes or unipolar electrodes to can.

Some embodiments of the neural stimulator 213 in FIG. 2 have eight electrical contacts. As illustrated in FIG. 10, four of the contacts are used for CRM sensing electrodes 1041, two of the contacts are used to sense action potentials in nerves 1040, and two of the contacts are used to stimulate nerves 1039. Other embodiments may be used. For example, some nerves are stimulated using tripolar electrodes. Fewer CRM sensing electrodes 1041 may be used to accommodate more neural stimulation electrodes. Neural sense electrodes could be designed into the cuff as shown, or as separate cuffs. The electrodes for neural therapy could also be used for neural sensing or CRM sensing. CRM sensing could be narrow field vector sensing between pairs of electrodes on the lead or could be wide field vector sensing between lead electrodes and can. Narrow field vectors may have advantages in rate determination, whereas wide field vector may provide a surrogate for surface ECG.

Figure 11:
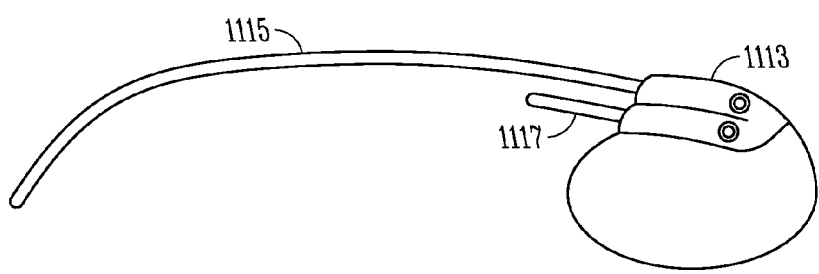
FIG. 11 illustrates an embodiment of an implantable neural stimulation device with a neural stimulation lead and a separate sensing stub lead used to remotely detect cardiac activity.

FIG. 11 illustrates an embodiment of an implantable neural stimulation device 1113 with a neural stimulation lead 1115 and a separate sensing stub lead 1117 used to remotely detect cardiac activity. The neural stimulation lead 1115 may include the cuff design illustrated in FIG. 10, for example.

Figure 12A:
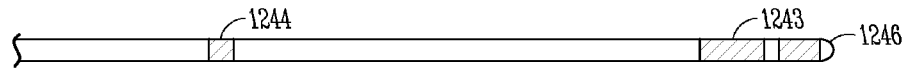
FIGS. 12A-12B illustrate an embodiment of a device with narrow field vector sensing capabilities.
Figure 12B:
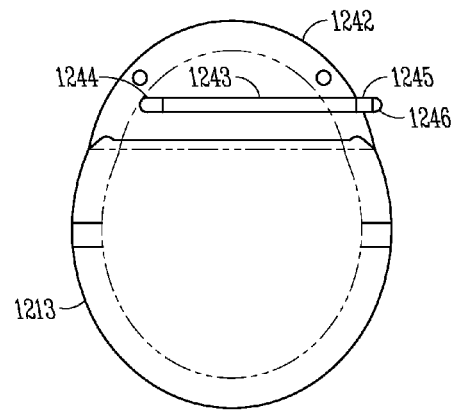

Various embodiments incorporate the CRM sensing electrode into a port plug. FIGS. 12A-12B illustrate an embodiment of a device 1213 with narrow field vector sensing capabilities using a port electrode and can. The device 1213 includes a header 1242 configured to receive a stub lead 1243. The stub lead and header have an electrical contact 1244. The illustrated stub lead includes a retention cuff 1245 and a sensing electrode 1246.

Figure 13:
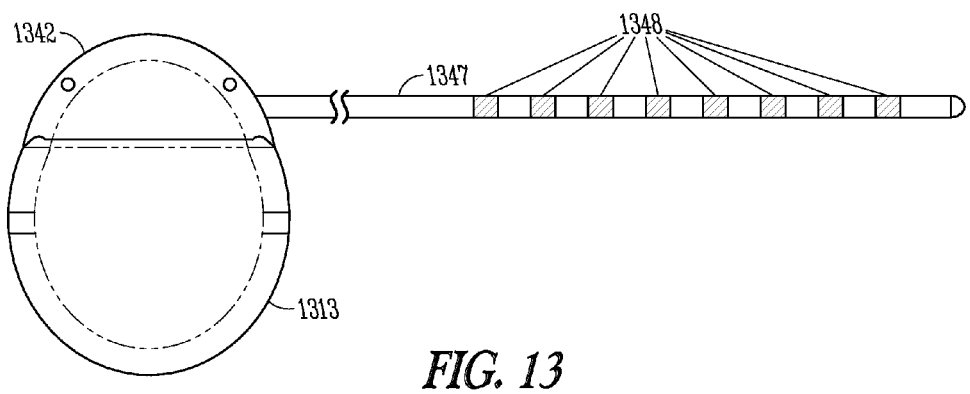
FIG. 13 illustrates an embodiment of a device with wide field vector sensing capabilities.

Various embodiments place the CRM sensing electrode or electrodes on a longer lead body in order to allow for wider field sensing. FIG. 13 illustrates an embodiment of a device 1313 with wide field vector sensing capabilities using a distal lead electrode and can. The illustrated device includes a header configured to receive the sensing lead 1347 with one or more sensing electrode(s) 1348. The sensing lead 1347 may tunnel next to the neural therapy lead or elsewhere in the body.

A common platform for both a stand-alone neural device and a combination neural and CRM device can be designed if remote CRM sensing capabilities are available. For example, the A or LV port may be modified for use as the neural output and the RV port may be maintained for sensing. The RV port could be connected to a small "stub" lead with a sensing electrode that allows for a narrow field vector sensing. A longer lead with a sensing electrode could also be placed in the RV port for a wider field vector sensing. The lead could be tunneled to any place under the skin and is not placed inside the cardiac tissue.

A sensing electrode could be incorporated into a stub lead or into the port itself in order to facilitate remote ECG sensing. Depending on the gain and signal to noise ratio, the remote ECG sensing could be used by a remote cardiac rate determiner, a remote R-wave detector or more.

Remotely determining rate may allow rate feedback to be part of a closed-loop neural stimulation therapy. By way of example and not limitation, neural stimulation could be applied only when the average rate has been above a threshold for a period of time. As R-waves have the highest amplitude in the ECG signal, the R-waves can be remotely sensed to determine rate. The present subject matter is not limited to using R-waves, as other waves (e.g. T-waves) may be detected and used to determine rate.

Figure 14:
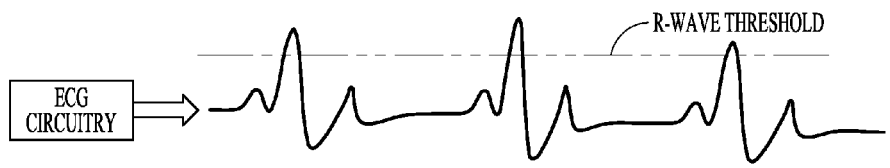
FIG. 14 illustrates remote cardiac R-wave detection for remote cardiac rate determination, according to various embodiments.

FIG. 14 illustrates remote cardiac R-wave detection for remote cardiac rate determination, according to various embodiments. A threshold crossing method can be applied to identify R-waves, which enables the determination of heart rate, average heart rate, HRV, and the like. More complex algorithms can be used to identify QRS components and AV delays and other diagnostics (see, for example, Yun-Chi Yeh and Wen-June Wang, "QRS Complexes Detection for ECG Signal: The difference operation method." Computer Methods and Programs in Biomedicine, Volume 91, Issue 3 (September 2008), Pages 245-254.)

Figure 15:
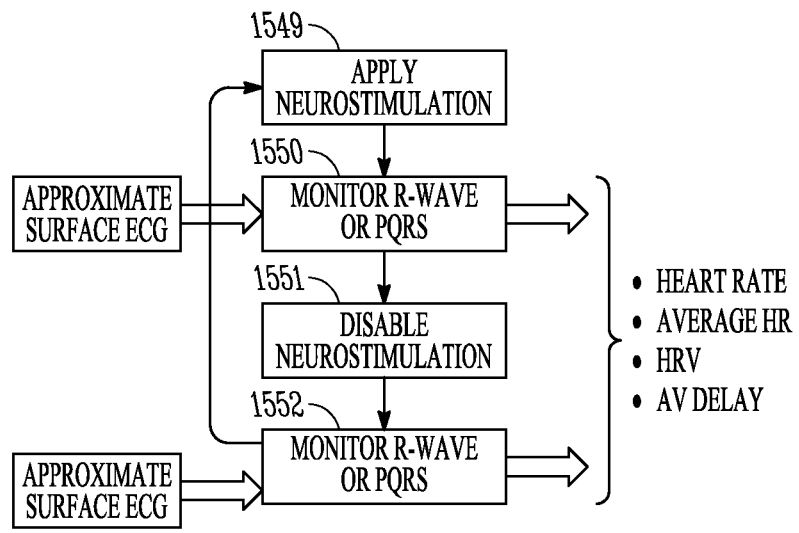
FIG. 15 illustrates an embodiment of a method for monitoring heart rate for feedback to a neural stimulation therapy.

FIG. 15 illustrates an embodiment of a method for monitoring heart rate for feedback to a neural stimulation therapy. The illustrated embodiment determines heart rate during time periods with neural stimulation and time periods without neural stimulation. For example, some embodiments apply neural stimulation with a duty cycle (e.g. an ON portion of approximately 10 seconds for each minute and an OFF portion of approximately 50 seconds). Thus, in the illustrated embodiment, neural stimulation is applied for about 10 seconds at 1549. As represented at 1550, the number of R-waves or PQRS waves are identified during these ten seconds of applied neural stimulation. At 1551, after the 10 seconds of neural stimulation, the neural stimulation is disabled for about 50 seconds. As represented at 1552, the number of R-waves or PQRS waves are identified during the period of disabled neural stimulation, before neural stimulation is again applied at 1549. The remote sensing of cardiac activity using electrodes provides an approximation of a surface ECG. The overall heart rate (HR) can be calculated, as well as the heart rate during periods of applied neural stimulation ($HR_{10}$) and periods without neural stimulation ($HR_{50}$). Each of these heart rates can be averaged over various predetermined periods of time. For example, the overall heart rate (HR) may be averaged over each minute, over a fraction of the minute, or over multiple minutes. The heart rate during periods of applied neural stimulation ($HR_{10}$) may be averaged over the entire duration of a neural stimulation episode (e.g. 10 seconds), over a fraction of each neural stimulation episode, or over multiple neural stimulation episodes. The heart rate periods without neural stimulation ($HR_{50}$) may be averaged over the entire duration of an episode of disabled neural stimulation (e.g. 50 seconds), over a fraction of each episode of disabled neural stimulation, or over multiple episodes of disabled neural stimulation. Additionally, HRV may be determined over a period that includes both times with and without neural stimulation (illustrated in the figure as HRV), over a period of time only when neural stimulation is applied (illustrated in the figure as $HRV_{10}$), or over a period of time only when neural stimulation is not applied (illustrated in the figure as $HRV_{50}$). The trending of heart rate, HRV, AV Delay, and the like can be performed using heart sounds or remote ECG analysis.

Figure 16:
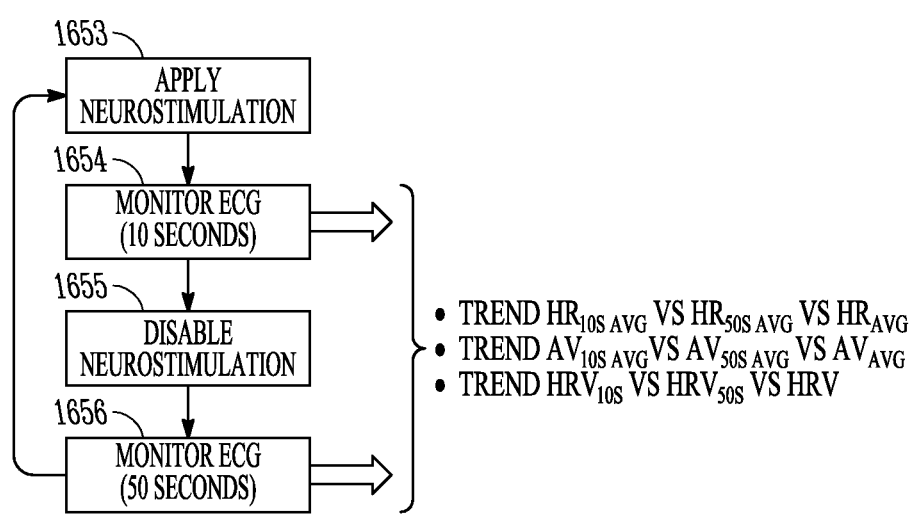
FIG. 16 illustrates an embodiment of a method for trending heart rate information for a neural stimulation therapy.

FIG. 16 illustrates an embodiment of a method for trending heart rate information for a neural stimulation therapy. In the illustrated embodiment, neural stimulation is applied for about 10 seconds at 1653. As represented at 1654, the ECG is monitored to identify the number of R-waves or PQRS waves during these ten seconds of applied neural stimulation. At 1655, after the 10 seconds of neural stimulation, the neural stimulation is disabled for about 50 seconds. As represented at 1656, the ECG is monitored to identify the number of R-waves or PQRS waves during the period of disabled neural stimulation, before neural stimulation is again applied at 1653.

The overall heart rate (FIR) can be calculated, as well as the heart rate during periods of applied neural stimulation ($HR_{10}$) and periods without neural stimulation ($HR_{50}$). Each of these heart rates can be averaged over various predetermined periods of time. For example, the overall heart rate (HR) may be averaged over each minute, over a fraction of the minute, or over multiple minutes. The heart rate during periods of applied neural stimulation ($HR_{10}$) may be averaged over the entire duration of a neural stimulation episode (e.g. 10 seconds), over a fraction of each neural stimulation episode, or over multiple neural stimulation episodes. The heart rate periods without neural stimulation ($HR_{50}$) may be averaged over the entire duration of an episode of disabled neural stimulation (e.g. 50 seconds), over a fraction of each episode of disabled neural stimulation, or over multiple episodes of disabled neural stimulation. Additionally, HRV may be determined over a period that includes both times with and without neural stimulation (HRV), over a period of time only when neural stimulation is applied ($HRV_{10}$), or over a period of time only when neural stimulation is not applied ($HRV_{50}$). The trending of heart rate, HRV, AV Delay, and the like can be performed using heart sounds or remote ECG analysis.

Figure 17:
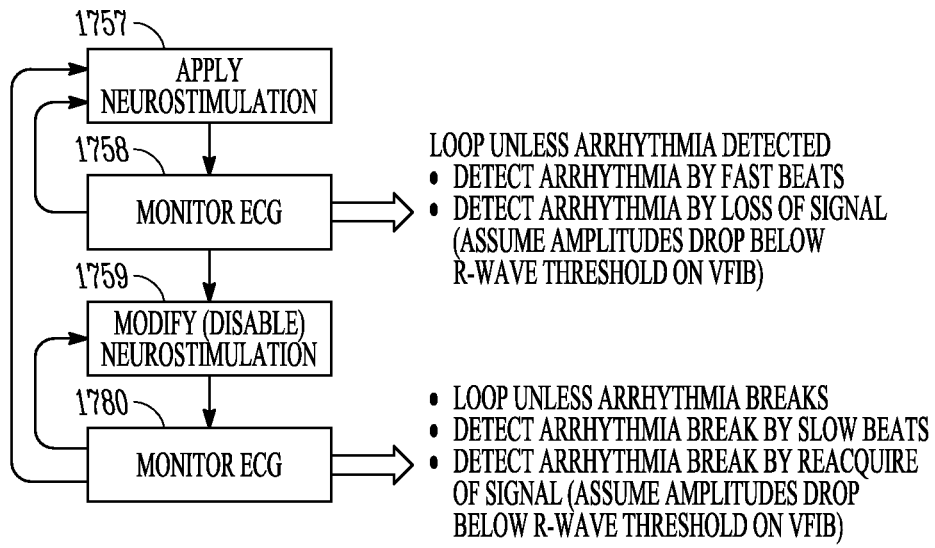
FIG. 17 illustrates an embodiment of a method for detecting arrhythmia.

According to various embodiments, a neural stimulation therapy is altered or suspended upon detection of an arrhythmia. FIG. 17 illustrates an embodiment of a method for detecting arrhythmia. At 1757, neural stimulation is applied for a period of time. During the period of time with neural stimulation, the electrical cardiac activity of the heart (e.g. ECG) is remotely monitored to detect for an arrhythmia, as represented at 1758. An arrhythmia may be detected by fast beats or by a loss of signal caused by the amplitudes of the sound signal dropping below the R-wave threshold during fibrillation. If no arrhythmia is detected, the illustrated method returns back to 1757 to continue the neural stimulation. At 1759, in response to a detected arrhythmia, the neural stimulation is modified or disabled. After modifying or disabling the neural stimulation, the electrical cardiac activity of the heart (e.g. ECG) is remotely monitored to determine if the arrhythmia breaks. If the arrhythmia continues, the illustrated method returns back to 1757. An arrhythmia break may be detected by slow beats, or by reacquiring a signal caused by the sound signal amplitude rising above the R-wave threshold after the arrhythmia breaks.

Figure 18:
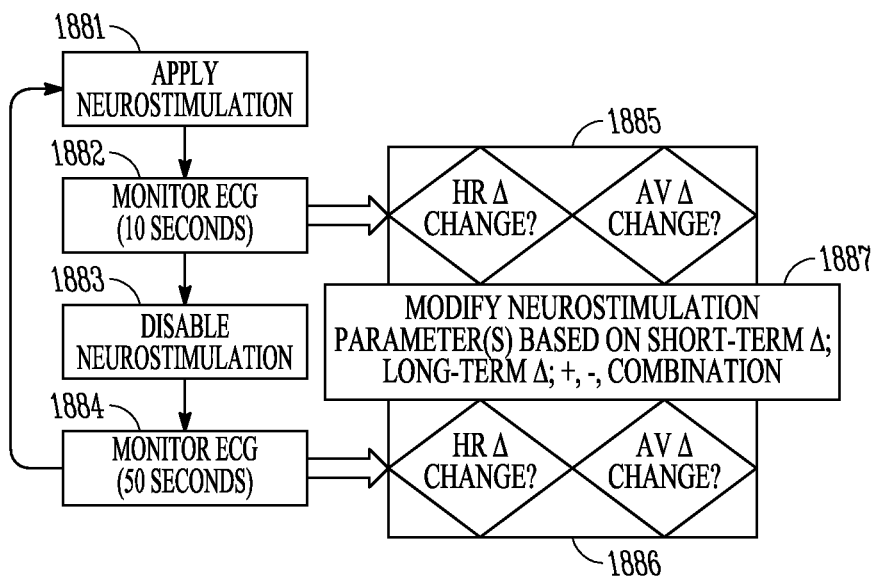
FIG. 18 illustrates an embodiment of a method for modulating a neural stimulation therapy.

FIG. 18 illustrates an embodiment of a method for modulating a neural stimulation therapy. For example, some embodiments apply neural stimulation for approximately 10 seconds for each minute. Thus, in the illustrated method, neural stimulation is applied for about 10 seconds at 1881. As represented at 1882, the number of detected R-waves is identified during these ten seconds of applied neural stimulation. At 1883, after the 10 seconds of neural stimulation, the neural stimulation is disabled for about 50 seconds. As represented at 1884, the number of detected R-waves is identified during the period of disabled neural stimulation, before neural stimulation is again applied at 1881. At 1885, a heart range change or an AV interval change is determined using the R-waves detected during the neural stimulation; and at 1886, a heart rate change or AV interval change is determined using the R-waves detected during times without neural stimulation. These changes are used to modify the neural stimulation, as generally illustrated at 1887. The modification to the neural stimulation may be based on short term changes, long term changes, or a combination of both short and long term changes. The modification of the neural stimulation can be based on response to physiological need (exercise, stress) or need to change dosing due to change in health status (lower heart rate due to better heart failure status). By way of example, and not limitation, some embodiments deliver neural stimulation that does not significantly alter heart rate. The therapy intensity (e.g. amplitude of the stimulation signal) may be reduced if the neural stimulation is consistently associated with an undesired heart rate change; or if an acute change in heart rate occurred during the latter portion of the ON time, the duration of the ON time could be altered or the intensity of the therapy (e.g. amplitude of the stimulation signal) may be reduced during the latter portion of the ON time. In some embodiments, a determination of a long term change in heart rate (e.g. lower heart rate due to improvement in heart failure) causes the device to change to a maintenance dose mode of therapy (e.g. delivering therapy for only a couple of hours a day). Various embodiments monitor for a divergence between the chronic average heart rate during the ON period and the chronic average heart rate during the OFF period, or other unexpected things, that may require a different therapy response. More complex algorithms can be used to identify QRS components, P-wave, T-wave and AV Delays. HRV diagnostic information can be obtained by, monitoring, storing and analyzing the intervals between R-wave detections. Some CRM devices use timing between R-waves to provide HRV and other HF diagnostics. R-waves can be determined from remotely-sensed ECG.

Some neural stimulation devices alter the neural stimulation therapy for cardiac pacing. Thus, if a neural stimulator and a CRM device are not designed to communicate with each other, then the neural stimulator includes a remote cardiac pace detector. Pace detection may be useful in an independent neural stimulation system implanted in an individual who also has a CRM device implant.

Figure 19:
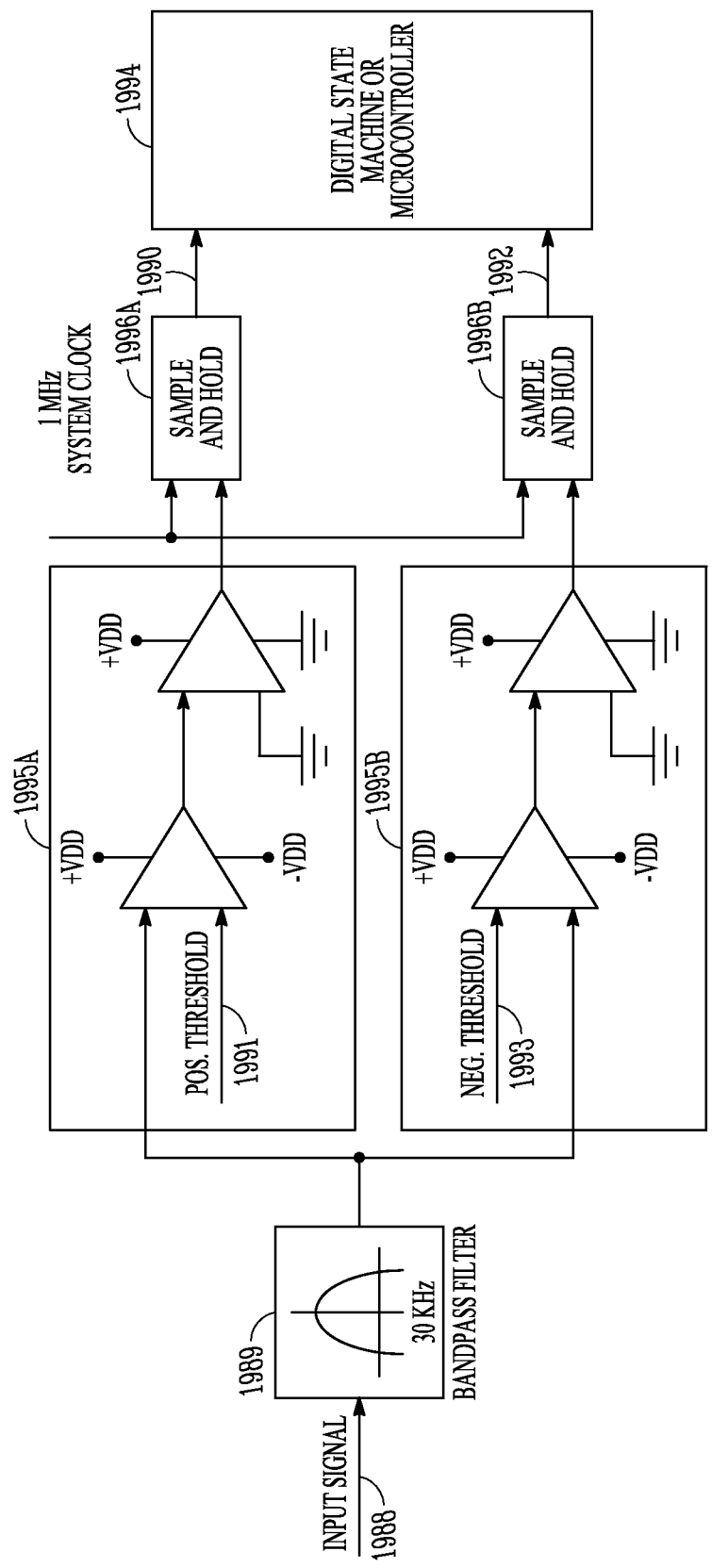
FIG. 19 illustrates an embodiment of remote cardiac pace detection circuitry.

FIG. 19 illustrates an embodiment of remote cardiac pace detection circuitry. The input signal 1988 comes from sense electrodes, and passes through a bandpass filter 1989 illustrated with a center frequency of approximately 30 KHz. The pace detection circuitry creates two detection signals. A first detection signal 1990 is generated when the rising edge of a pace pulse passes through the bandpass filter at a level greater than the positive threshold 1991. A second detection signal 1992 is generated when the falling edge of a pace pulse passes through the bandpass filter at a level more negative than the negative threshold 1993. The combination of the two detection signals, as received by the digital state machine or microcontroller 1994, results in a pace detection. For each of the illustrated detection signals, the illustrated circuit includes a cascaded amplifier 1995A and 1995B that functions as a comparator, and a sample and hold circuit 1996A and 1996B clocked by a 1 MHz system clock.

Figure 20:
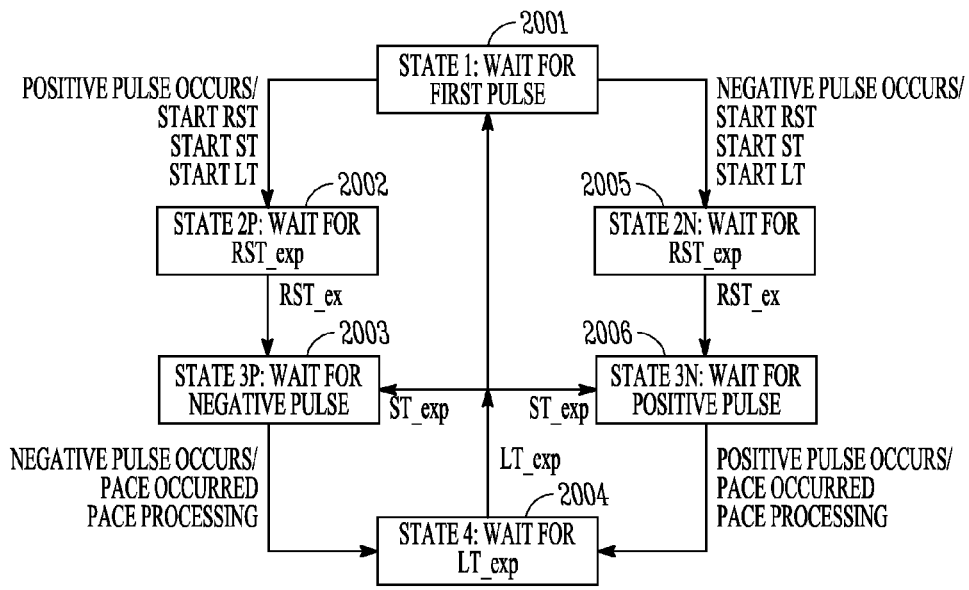
FIG. 20 illustrates a flow diagram of an embodiment for detecting pulses using the pace detection circuitry illustrated in FIG. 19.

FIG. 20 illustrates a flow diagram of an embodiment for detecting pulses using the pace detection circuitry illustrated in FIG. 19. State 1, represented at 2001, is a state in which the circuit waits for the first pulse. If the first pulse is positive, three timers are started and the circuit enters State 2P, represented at 2002. These timers include a first timer identified as a really short timer (RST), a second timer identified as a short timer (ST), and a third timer identified as a long timer (LT). The names given to these timers represent a manner of degree, and are not intended to be limiting. State 2P is a state in which the circuit waits for the first timer (RST) to expire. The end of the time represented by RST represents a beginning of a time frame for an expected negative pulse to occur after the positive pulse sensed at 2001. Once the first timer expires, the circuit enters State 3P, represented at 2003, which is a state in which the circuit waits for the expected negative pulse. If the second timer (ST) expires without a negative pulse, the circuit returns to State 1 at 2001. If a negative pulse occurs, the circuit enters State 4, represented at 2004, which is a state in which the circuit waits for the expiration of the third timer (LT). When the third timer (LT) expires, the circuit returns to State 1. If the first pulse is negative, three timers are started and the circuit enters State 2N, represented at 2005. These timers include a first timer identified as a really short timer (RST), a second timer identified as a short timer (ST), and a third timer identified as a long timer (LT). The names given to these timers represent a manner of degree, and are not intended to be limiting. Also, the timers associated with the negative pulse may or may not be the same as the timers associated with the positive pulse. State 2N is a state in which the circuit waits for the first timer (RST) to expire. The end of the time represented by RST represents a beginning of a time frame for an expected positive pulse to occur after the negative pulse sensed at 2001. Once the first timer expires, the circuit enters State 3N, represented at 2006, which is a state in which the circuit waits for the expected positive pulse. If the second timer (ST) expires without a positive pulse, the circuit returns to State 1 at 2001. If a positive pulse occurs, the circuit enters State 4, represented at 2004, which is a state in which the circuit waits for the expiration of the third timer (LT). When the third timer (LT) expires, the circuit returns to State 1. This algorithm is looking for pulses of opposite polarity that occur between RST and ST apart, where RST and ST are the respectively the minimum and maximum expected pacing pulse widths. Once a pace is detected, the algorithm waits a time corresponding to the third timer (LT) from the beginning of the pace before looking for another pace, where the time corresponding to the third timer (LT) is the expected minimum pacing interval.

Various embodiments remotely detect which heart chamber is being paced. In some embodiments, the pacemaker is programmed with different pacing pulse widths for each chamber (e.g. 0.40 ms for an atrial pace, 0.50 ms for a right ventricular pace and 0.45 for a left ventricular pace). In this embodiment, for example, multiple short timers (ST in the above algorithm) may be implemented to identify each specific programmed pulse width. In some embodiments, input from a remote ECG sensor is used to determine whether the detected pace pulse is associated in time with a P-wave or an R-wave on the ECG.

To account for dual-chamber pacing and CRT pacing as well as rate-responsive pacing or loss of capture, more complex algorithms can be used to identify QRS components, P-wave, T-wave and AV Delays via remote ECG analysis. A wide vector between the neural lead and the can of the implanted neural stimulator or a small vector from a stub lead to the can of the implanted neural stimulator can be used to show the QRS components under the proper gain. HRV diagnostic information can be obtained by monitoring, storing and analyzing the intervals between R-wave detections.

Figure 21:
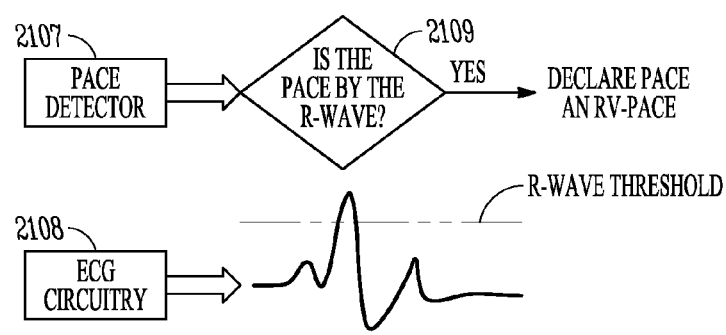
FIG. 21 illustrates an embodiment of a method for correlating a detected pace to a right ventricle pace.

According to various embodiments, the neural stimulator is programmed to know that the pacemaker is a single chamber device and therefore declare any detected pace as an RV-pace. Some embodiments declare any detected pace followed by an R-wave sense as a captured RV-pace. FIG. 21 illustrates an embodiment of a method for correlating a detected pace to a right ventricle pace. A pace is detected at 2107. The pace may be detected using the system illustrated in FIGS. 19-20. ECG circuitry 2108 remotely senses cardiac electrical activity, and the remotely sensed ECG may be used to determine an R-wave. As illustrated at 2109, if the pace occurs close in time to the sensed R-wave, then the RV-pace is declared. All other detected paces would be declared as a non-captured RV-pace. The neural stimulation therapy may be altered based on capture or non-capture. In embodiments that remotely sense an ECG and discriminate P-wave or determine cardiac cycle timing based on heart sounds, a detected pace may be assigned as a captured A-pace, non-captured A-pace, captured RV-pace or non-captured RV-pace.

Figure 22:
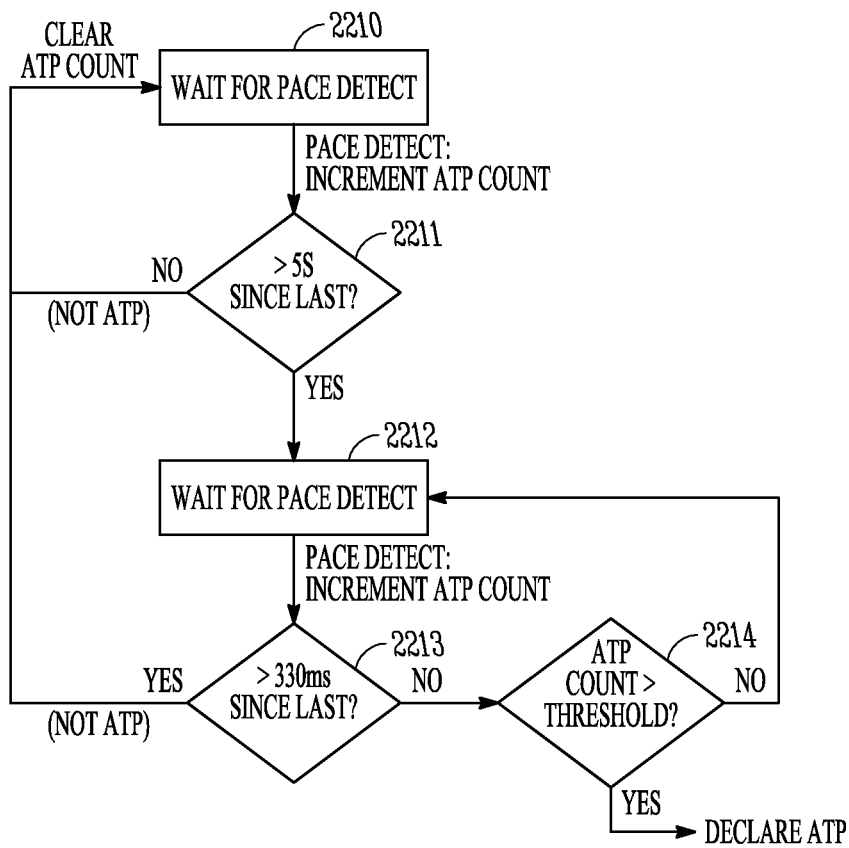
FIG. 22 illustrates an embodiment of a method for detecting antitachycardia pacing (ATP).

FIG. 22 illustrates an embodiment of a method for detecting antitachycardia pacing (ATP). Some embodiments assume that no cardiac pacing will occur for at least 5 seconds prior to an ATP burst since the patient would be in an arrhythmia. As illustrated, the embodiment waits for a detected pace at 2210. When the pace is detected, an antitachycardia pacing (ATP) count is incremented. At 2211, it is determined if there has been at least 5 seconds (or other predetermined period) since the last pace. If there has not been at least 5 seconds since the last pace, then it is assumed that the patient is not in an arrhythmia, the ATP count is cleared and the process returns to 2210. If there has been at least 5 seconds since the last pace, then the process waits for the next pace detect at 2212. When the next pace is detected, the ATP count is incremented. At 2213, it is determined if there has been at least 330 ms since the last pace. If there has been at least 330 ms (or other predetermined period) since the last pace, then it is determined that ATP is not present, the ATP count is cleared, and the process returns to 2210. If there has not been at least 330 ms (or other predetermined period), it is determined at 2214 whether the ATP count is greater than a threshold. If the ATP count is greater than the threshold, an ATP is declared. If the ATP count is not greater than the threshold, then the process returns to 2212 to wait for another subsequent pace that may be part of antitachycardia pacing. ATP may be referred to as overdrive pacing. Other overdrive pacing therapies exist, such as intermittent pacing therapy (IPT), which may also be referred to as a conditioning therapy. Various embodiments detect an overdrive pacing therapy and modify neural stimulation if overdrive pacing is detected.

Figure 23:
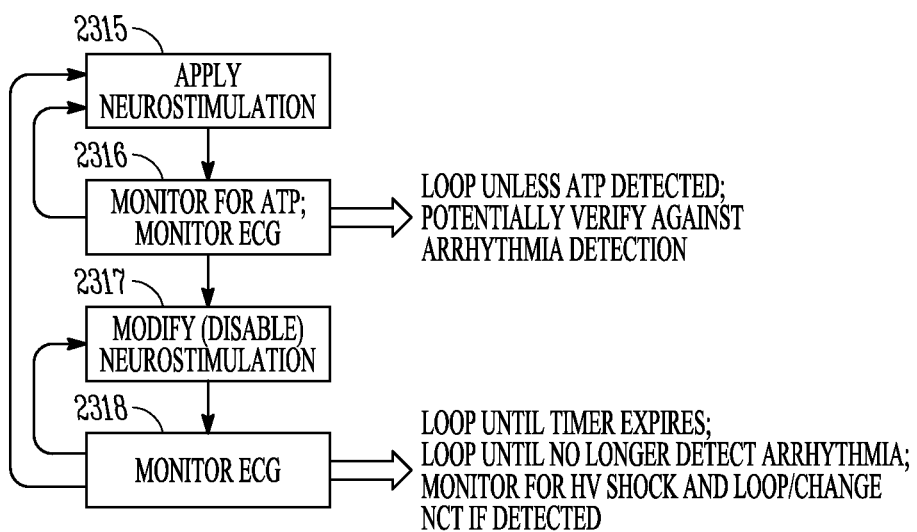
FIG. 23 illustrates an embodiment of a method that uses antitachycardia pacing as an input to a neural stimulation therapy.

FIG. 23 illustrates an embodiment of a method that uses antitachycardia pacing as an input to a neural stimulation therapy. A neural stimulation therapy is applied at 2315, and at 2316 the remotely sensed cardiac activity (e.g. ECG) is monitored for antitachycardia pacing. If antitachycardia pacing is detected, the neural stimulation is disabled or modified as illustrated at 2317 until a predetermined trigger to begin the normal neural stimulation again. The trigger may be an expired timer. Some embodiments monitor ECG 2318 while the neural stimulation is disabled or modified, and begin the normal stimulation when an arrhythmia is no longer detected. Some embodiments monitor for a high voltage shock and return to delivering neural stimulation after the high voltage shock.

Other embodiments to incorporate information from a rate sensor rather than assuming that no cardiac pacing will occur for at least 5 seconds prior to an ATP burst. In some embodiments, the ATP detection algorithm is invoked after the detected rate from the remote rate sensor surpasses a remote tachy detection threshold, and the determination of whether it has been 5 seconds since the last pace could be removed from the remote ATP detection algorithm. Additional information from an activity sensor such as an accelerometer could further be used to refine the algorithm to screen out rate responsive pacing.

The sensitivity and the specificity of remote CRM information can be increased by using information obtained from multiple sources (e.g. blended remote CRM information). Various embodiments blend inputs from remote cardiac R-wave sensors, remote cardiac rate determiners, activity sensors or other sensors. Various embodiments blend cardiac sense response and cardiac pace response as well as inputs from remote cardiac R-wave sensors, remote cardiac rate determiners, activity sensors or other sensors. The pace location identification approach is one example. Some embodiments combine inputs from the leads and the accelerometer to remotely detect rate. For example, the detected ECG cardiac activity may be blended with the detected heart rate information using an accelerometer (indicative of the mechanical function of the heart). Electrical-mechanical dyssynchrony is a signature of heart failure and provides diagnostic information for a device designed to treat heart failure. The detected cardiac activity may be used to ascertain heart sounds.

Some neural stimulation therapies alter the therapy based on cardiac sensing and pacing. For example, some embodiments synchronize withhold or alter a neural stimulation therapy on a remotely detected sense, a remotely detected RV-sense, or remotely detected other chamber sense. Some embodiments apply withhold or alter a neural stimulation therapy when the sensed cardiac rate is above a lower rate level (LRL) (indicative of a physiological need such as stress, exercise, and the like). Some neural stimulation or autonomic modulation therapies may acutely decrease heart rate. An embodiment includes a LRL cutoff below which those therapies would be suspended to avoid lowering an already low heart rate. Some embodiments provide a maximum sensing rate cutoff for delivering these therapies to avoid interactions between high intrinsic rates and a therapy that can alter conduction. Some embodiments deliver a short term neural stimulation therapy immediately after a detected premature ventricular contraction (PVC) to alter conduction. Some embodiments apply, withhold or alter a neural stimulation therapy when the average resting heart rate has changed by a certain amount (due to remodeling, worsening heart failure, change in drug regimen, and the like). Some embodiments apply, withhold or alter neural stimulation therapy when average AV Delay (from remote ECG analysis) or average left ventricular ejection time (LVET) (from heart sound analysis) changes over time. Some embodiments apply, withhold or alter neural stimulation therapy upon remote arrhythmia detection (sensing rate above an arrhythmia threshold).

By way of example, one embodiment provides rapid therapy titration for a neural stimulation therapy when the sensing rate is above a certain rate. Some implementations of vagus nerve stimulation affect cardiac rate. As such, cardiac rate may be used as an input for therapy titration and, if cardiac heart rate is available via remote sensing, then therapy could be automatically titrated. Various embodiments titrate the therapy to find the highest tolerable therapy that increases heart rate, lengthens AV delay and the like, or to find the highest therapy that does not alter or significantly alter heart rate, AV delay and the like.

Figure 24:
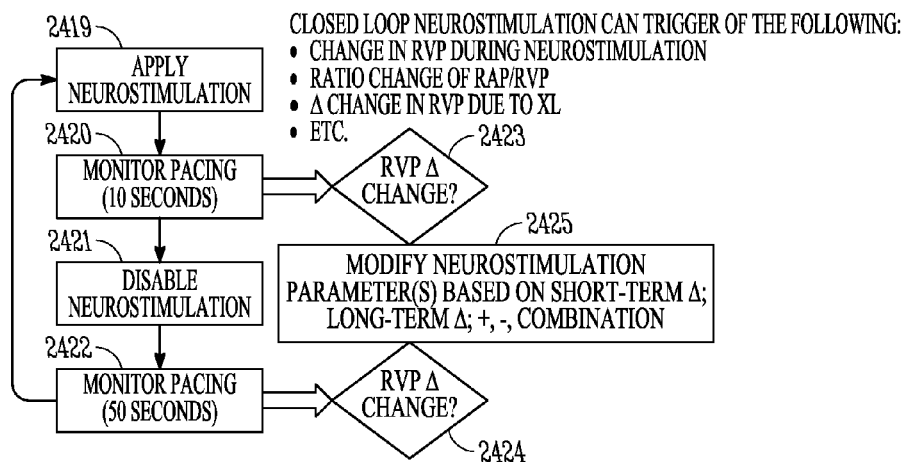
FIG. 24 illustrates various embodiments of closed loop neural stimulation that use detected pacing as an input.

FIG. 24 illustrates various embodiments of closed loop neural stimulation that use detected pacing as an input. Various neural stimulation therapies involve intermittent neural stimulation (e.g. a programmed duty cycle with a programmed period of neural stimulation followed by a programmed period without neural stimulation). Some embodiments, by way of example and not limitation, provide about 10 seconds of neural stimulation followed by about 50 seconds without neural stimulation. At 2419, neural stimulation is applied (e.g. about 10 seconds of stimulation). At 2420, pacing is monitored for the period of time when neural stimulation is applied. The neural stimulation is disabled at 2421, and pacing is monitored during the period of time without neural stimulation (e.g. about 50 seconds without neural stimulation). At 2423, the process determines the change in the detected right ventricle pacing during the period when neural stimulation is applied. At 2424, the process determines the change in the detected right ventricle pacing during the period when neural stimulation is not applied. Neural stimulation parameter(s) can be modified based on short-term changes, long-term changes, or combinations of short-term and long-term changes. By way of example and not limitation, neural stimulation therapy can trigger off of a change in detected right ventricle paces during neural stimulation, a ratio change if right atrium pacing to right ventricle pacing, or a change in right ventricle pacing corresponding to accelerometer activity.

Some embodiments synchronize, withhold or alter neural stimulation therapy on a remotely detected pace, remotely detected RV-pace, or remotely detected other chamber pace. Some embodiments apply, withhold or alter neural stimulation therapy when a pacing rate is above a LRL for a sensed cardiac rate (indicative of a physiological need such as stress, exercise, etc). Some neural stimulation or autonomic modulation therapies may acutely decrease heart rate. An embodiment includes a LRL cutoff below which those therapies would be suspended to avoid lowering an already low heart rate. Some embodiments provide a maximum sensing rate cutoff for delivering these therapies to avoid interactions between high intrinsic rates and a therapy that can alter conduction. Some embodiments deliver a short term neural stimulation therapy immediately after a detected premature ventricular contraction (PVC) to alter conduction. Some embodiment apply, withhold or alter a neural stimulation therapy when x % of the cardiac cycles have been paced for a y period of time. For example, a change in AV Delay may cause more or less RV pacing. It may be appropriate to change neural stimulation therapy if there is an extended period of pacing or an extended period of not pacing. Some embodiments apply, withhold or alter neural stimulation when always pacing at rest which may indicate remodeling, worsening heart failure, a change in a drug regimen, and the like. Some embodiments apply, withhold or alter neural stimulation upon a remote ATP detection. Some embodiments provide a first heart failure therapy involving cardiac resynchronization therapy (CRT) and a second heart failure therapy involving neural stimulation. The system may be programmed so that CRT has priority over the neural stimulation. If the loss of left ventricular pacing or biventricular pacing is lost, then the neural stimulation is suspended, or an AV parameter may be changed. The dose of the neural stimulation may be altered if the system determines that the loss of pacing occurs during the latter portion of the ON portion of the neural stimulation period. The neural stimulation amplitude may be adjusted (e.g. ramped up) during the initial portion of the ON portion if loss of CRT is detected. Rather than using x % to apply, withhold or alter the neural stimulation therapy, some embodiments use another metric, such as a programmed number of cycles (e.g. four cycles) without or without a pace.

Respiration creates sounds that may be picked up by an accelerometer placed close to the trachea. The accelerometer can be either in the can or on the vagal nerve lead. The location of the neural stimulation can and lead may not be conducive to using the minute ventilation system currently employed in CRM products.

Figure 25:
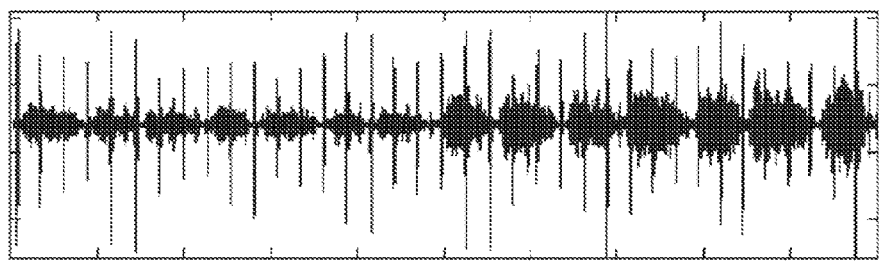
FIG. 25 illustrates an example of band-pass filtered tracheal sound, such as may be used in various embodiments.

Breathing, snoring and other breathing noises have frequency components with the highest frequency about 2 KHz. Sampling rates of twice that or more are required. Bandpass filtering from 200 Hz to 1500 Hz will cover most of the spectrum of interest. Narrower bandpass filtering of 250 Hz to 600 Hz may provide a better signal to noise ratio in the intended implanted environment. Also, multiple narrower bandpass filtering may provide unique information about respiration such as depth of breath, or distinguishing cough and voice. FIG. 25 illustrates an example of bandpass filtered tracheal sound (75 Hz to 600 Hz), as was illustrated by A. Yadollahi and Z. M. K. Moussavi, "Acoustical Respiratory Flow", IEEE Engineering in Medicine and Biology, January/February 2007, pages 56-61. Various embodiments may use a bandpass filtered tracheal sound similar to that illustrated in FIG. 25.

Figure 26:
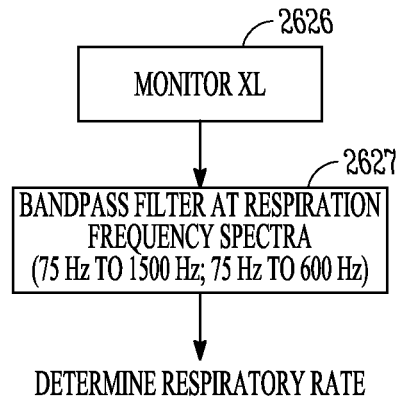
FIG. 26 illustrates an embodiment of a method for filtering tracheal sound.

FIG. 26 illustrates an embodiment of a method for filtering tracheal sound. At 2626, an accelerometer is monitored to provide an acoustic signal, and this acoustic signal is passed through a bandpass filter to pass the acoustic signal corresponding to respiratory frequencies. In some embodiments, the bandpass filter passes frequencies from approximately 75 Hz to approximately 1500 Hz. In some embodiments, the bandpass filter passes frequencies from approximately 75 Hz to 600 Hz.

Figure 27:
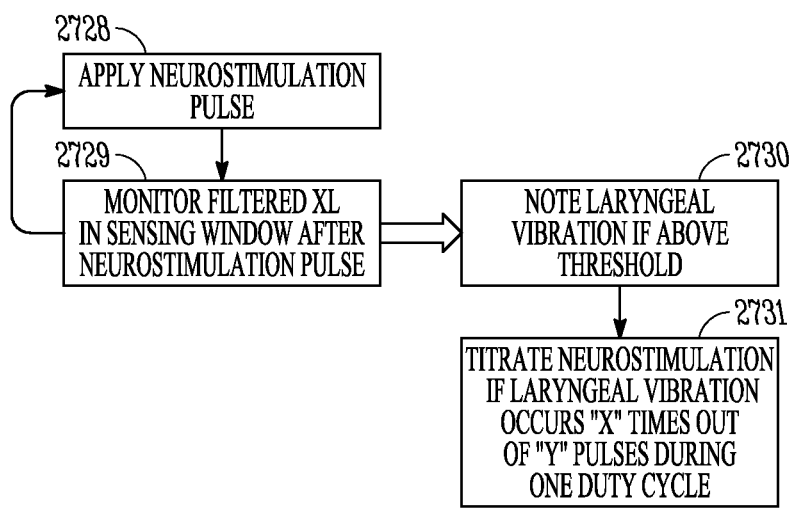
FIG. 27 illustrates an embodiment of a method for titrating neural stimulation.

FIG. 27 illustrates an embodiment of a method for titrating neural stimulation. A neural stimulation therapy is applied at 2728. At 2729, a bandpass filtered accelerometer signal is monitored in a sensing window (a period of time) after the neural stimulation pulse. At 2730, the filtered accelerometer signal is used to determine whether laryngeal vibration is above a threshold. As illustrated at 2731, some embodiments titrate the neural stimulation therapy if the laryngeal vibration occurs "x" times out of "y" pulses during one duty cycle. In an embodiment where neural stimulation is delivered with an ON/OFF cycle and at 20 Hz for 10 seconds for every ON period, 200 pulses are delivered every 10 second dosing cycle. Laryngeal vibration may be detected after only half, or other value, of the pulses in a dosing cycle, or a patient may tolerate therapy if laryngeal vibration occurs in response to only 10 or 50 of those 200 pulses. The present subject matter can work if laryngeal vibration occurs at all during the ON portion. Various embodiments automatically titrate neural stimulation down if the number of laryngeal vibration goes above the threshold.

Some neural stimulation therapies may be modulated or otherwise controlled based on breathing rate. For example, higher averaged breathing rate could indicate stress or exercise and the neuromodulation therapies could be enabled, modified, or disabled in response to a change in average breathing rate.

Some neural stimulation therapies may be modulated or otherwise controlled based on apneic event detection. For example, a breathing pattern indicative of Stokes-Cheney could trigger enabling, modifying, or disabling a neural stimulation therapy.

A number of methods have been proposed to detect apnea, particularly detecting apnea using tracheal sounds. One such approach is discussed in "Apnea Detection by Acoustical Means," Yadollahi, A.; Moussavi, Z.; Engineering in Medicine and Biology Society, 2006, EMBS '06, 28th Annual International Conference of the IEEE, Aug. 30 2006-Sep. 3 2006, Pages 4623-4626.

Some neural stimulation therapies may be modulated or otherwise controlled based on estimates of respiratory flow. Estimates of flow can be made using analysis of tracheal sounds. A number of methods have been proposed to estimate respiratory flow using tracheal sounds. One such approach is discussed in "A robust method for estimating respiratory flow using tracheal sounds entropy," Yadollahi, A; Moussavi, Z; M. K., Biomedical Engineering, IEEE Transactions, Volume 53, Issue 4, April 2006 Pages 662-668.

Sounds from the heart may interfere with efforts to analyze respiratory sounds. Respiratory sounds are almost free of the heart sounds effect at a frequency range over 300 Hz. However, there is overlap in the frequency ranges for where most of the heart sound energy occurs (20 Hz to 200 Hz) and for where most of the respiratory sound energy occurs (75 Hz to 600 Hz). Information about expiratory respiration can be lost if the respiratory sounds are analyzed at a frequency range over 300 Hz, whereas information about inspiratory respiration can be analyzed at higher frequencies (see Gavriely, N., Nissan, M., Rubin A. H. and Cugall, D. W. "Spectral characteristics of chest wall breath sounds in normal subject," Thorax, 11995, 50:1292-1300). Respiratory rate may be determined using the inspiratory sounds above 300 Hz since the respiratory sounds are mostly free of heart sounds at those rates, making analysis presumably easier. However, other respiratory information would not be available if using chest wall breath sounds. There may be some shift in the spectral pattern using sounds from the trachea and the paper. There may be some shift in the spectral pattern using sounds from the trachea and the may be enough information in the 300 Hz to 600 Hz frequency range to determine both respiratory rate and flow.

Implanted devices have means to detect cardiac activity. Electrical activity as determined from an ECG or sensing from intracardiac leads can be used to identify the QRS complex. The S1 heart sounds are correlated with the end of the QRS. Analysis of the respiratory sound could then blank or ignore the signal around the identified area for heart sound, or subtraction or other signal processing could be performed for that segment of the signal to account for the heart sound. Mechanical activity of the heart can be determined and similar, or complementary, signal processing of the respiratory signal can be performed.

Respiratory sensors may have a need to be calibrated for accuracy and can be calibrated with the use of one or more breaths under defined conditions. A "learning" mode for calibration may be incorporated within the implanted device to individualize the analysis of the respiratory sound to the patient. This learning mode can be physician-initiated or performed automatically by the device when certain criteria (e.g. meeting minimal activity).

Vagus nerve stimulation can elicit laryngeal vibration above a stimulation threshold. Laryngeal vibration may be a tolerable side effect whose presence indicates therapy is being delivered. Laryngeal vibration may be remotely detected using an accelerometer. An embodiment of a remote laryngeal vibration detector monitors the output of the accelerometer after each neural stimulation pulse. If there is a signal on the accelerometer, then the detector can declare laryngeal vibration.

Figure 28:
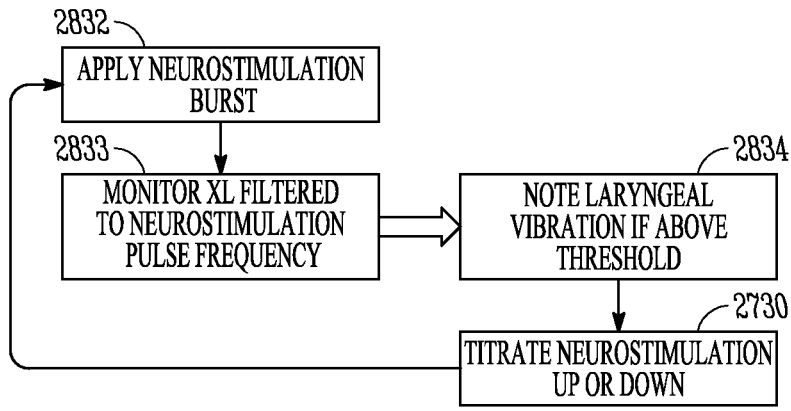
FIG. 28 illustrates an embodiment of a method for detecting laryngeal vibration by monitoring an accelerometer filtered to a neural stimulation frequency.

FIG. 28 illustrates an embodiment of a method for detecting laryngeal vibration by monitoring an accelerometer filtered to a neural stimulation frequency. At 2832, the neural stimulation burst is applied. The neural stimulation has a pulse frequency. At 2833, accelerometer data is filtered to the neural stimulation pulse frequency. If the laryngeal vibration is above a threshold, as determined at 2834, then the intensity of the neural stimulation therapy is titrated up or down at 2835.

Figure 29:
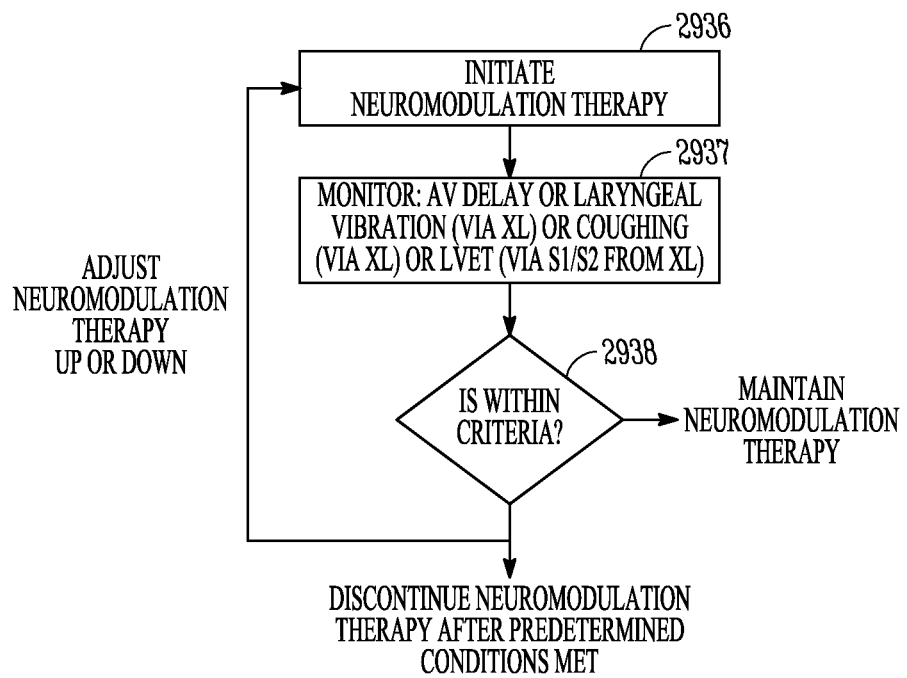
FIG. 29 illustrates an embodiment of a method for controlling neural stimulation.

FIG. 29 illustrates an embodiment of a method for controlling neural stimulation. A neural stimulation therapy is initiated at 2936. Accelerometer data is monitored at 2937 to determine AV delay, or laryngeal vibration, or coughing, or LVET. At 2938, it is determined if the accelerometer data is satisfying the criteria for the neural stimulation therapy. If it is, the neural stimulation is maintained. If it is not, then the neural stimulation therapy is adjusted in an effort to bring the monitored accelerometer data into compliance with the criteria for the neural stimulation therapy. If neural stimulation is provided to deliver a maximum tolerable amplitude, an example of criteria for neural therapy titration includes increasing amplitude until laryngeal vibration detection, continuing to increase amplitude until coughing is detected, reducing the amplitude a step, verifying laryngeal vibration is still detected, and ending titration. Assuming that laryngeal vibration indicates all nerve fibers have been captured, if neural stimulation is provided to deliver a lowest amplitude does with confirmation that therapy is being delivered, an example increases amplitude until laryngeal vibration is detected, and titration is ended. This may include detecting laryngeal vibration, decreasing amplitude until laryngeal vibration no longer is detect, increasing amplitude one step, and verifying laryngeal vibration to confirm therapy delivery. In some embodiments, this includes detecting coughing, decreasing amplitude until coughing is no longer detected, and verifying laryngeal vibration to confirm therapy delivery. Some embodiments increase amplitude until laryngeal vibration is detected, back down amplitude one step to provide a maximum amplitude dose without side effects, assuming therapy effective without need to laryngeal vibration to confirm therapy delivery. Some embodiments increase amplitude until laryngeal vibration is detected, back down amplitude one step, and confirm therapy effectiveness using a change in AV delay or a change in LVET. The neural stimulation therapy may be discontinued after predetermined conditions are met.

Some embodiments monitor the accelerometer and filter for signal with a frequency corresponding to neural stimulation (e.g. bandpass filter for a 20 Hz signal). If there is laryngeal vibration due to neural stimulation with a plurality of pulses where the frequency of the pulses is 20 Hz, then that vibration will be modulated at 20 Hz. The bandpass filtered 20 Hz signal could also be monitored only when neural stimulation is being delivered. Some embodiments compare the bandpass filtered signal with neural stimulation to the bandpass filtered signal without neural stimulation. If there is a 20 Hz signal on the accelerometer when neural stimulation is being delivered, then the detector can declare laryngeal vibration. The 20 Hz pulse frequency is an example. The bandpass filtering is tuned to the frequency of the pulse delivery. The frequency may be a programmable value and the filtering should automatically adjust to whatever the programmed frequency.

Figure 30:
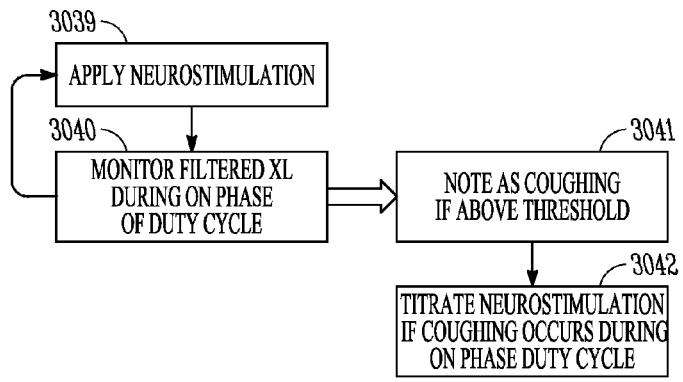
FIG. 30 illustrates an embodiment of a method for controlling neural stimulation using a filtered accelerometer signal monitored over a neural stimulation burst.

FIG. 30 illustrates an embodiment of a method for controlling neural stimulation using a filtered accelerometer signal monitored over a neural stimulation burst. Neural stimulation may be delivered with a duty cycle that includes an ON phase and an OFF phase. At 3039, a neural stimulation is applied during an ON phase of the duty cycle, and a filtered accelerometer signal is monitored during the ON phase of the duty cycle, as illustrated in 3040. At 3041, the filtered accelerometer signal is used to determine if coughing above a threshold is occurring. Various embodiments titrate neural stimulation if coughing occurs during the ON phase of the duty cycle. For example, the neural stimulation intensity may be reduced to avoid the cough.

Laryngeal vibration may be used to rapidly titrate a neural stimulation therapy. A laryngeal vibration detector may be used to automatically titrate therapy up or down based on whether there is vibration. This titration could be performed at the time of implant, at follow-up visits to a clinical setting, or in an ambulatory patient.

Figure 31:
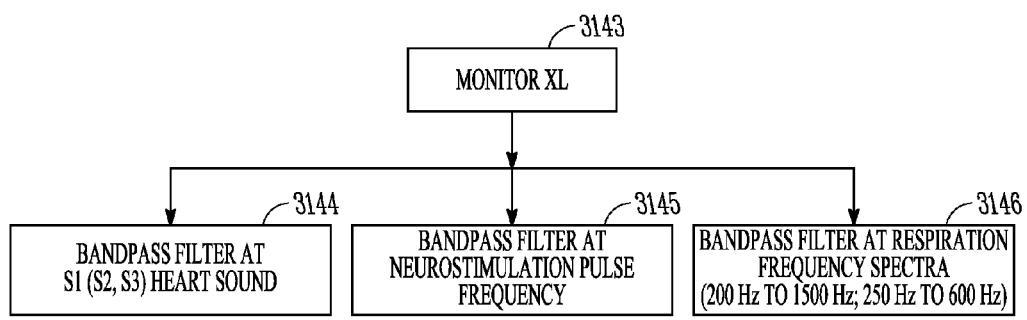
FIG. 31 illustrates an embodiment of a method for rapidly titrating neural stimulation therapy using accelerometer data.

FIG. 31 illustrates an embodiment of a method for rapidly titrating neural stimulation therapy using accelerometer data. As illustrated, different information can be obtained from one accelerometer based on how the output of the accelerometer is filtered. An accelerometer data signal is monitored at 3143. As illustrated at 3144, a bandpass filter corresponding to a heart sound (e.g. S1) is applied to the accelerometer data signal. This information can be used to determine heart rate and other information based on rate. As illustrated at 3145, a bandpass filter corresponding to a neural stimulation frequency is applied to the accelerometer data signal. This may be used to detect the laryngeal vibration attributed to neural stimulation. As illustrated at 3146, a bandpass filter corresponding respiratory frequencies is applied to the accelerometer data. This information can be used to titrate, initiate, or terminate neural stimulation.

Vagus nerve stimulation can elicit coughs above a stimulation threshold. Various embodiments use an elicited cough to automatically determine therapy levels. An accelerometer can be used to detect a vibration from a cough. Various embodiments of a remote cough vibration detector monitor the output of the accelerometer after each neural stimulation pulse. If there is a signal on the accelerometer during or immediately following neural stimulation pulse, then the detector can declare cough due to the neural stimulation therapy. Various embodiments of the remote cough vibration detector monitor the output of the accelerometer during the initial portion of the neural stimulation burst to determine cough. Some embodiments confirm the presence of cough. For example, if cough is detected two or more duty cycles in a row, then the presence of cough is confirmed.

Some embodiments use cough vibration to rapidly titrate a neural stimulation therapy. A cough vibration detector may be used to automatically titrate therapy up or down based on whether there is vibration. This titration could be performed at the time of implant, at follow-up visits to a clinical setting, or in an ambulatory patient. In various embodiments, rapid therapy titration is performed using a combination of inputs such as input from a cough vibration detector and input from a laryngeal vibration detector. For example, laryngeal vibration may be the marker for desired therapy but coughing is undesirable. In that case, therapy is titrated up to where a cough is detected and then backed off and laryngeal vibration is then verified. Rapid therapy titration could be performed using a rate determination sensor as well as a laryngeal vibration or cough detector.

Various embodiments provide physician-commanded titration, where titration is performed by the implanted device but under that manual initiation of the physician. Titration and physician monitoring of side effects may be performed by the physician where the physician manually programs the therapy intensity (e.g. amplitude) up or down. Some embodiments provide a one-button initiation of titration and monitoring of side effects.

Various embodiments provide daily titration, where the titration of therapy is performed automatically on a daily (or other periodic) basis. This allows the therapy intensity (e.g. amplitude) to be increased as a patient accommodates to the therapy. It may be desirable to drive therapy to the greatest tolerable level if the increased in the therapy intensity provides a more effective therapy.

Various embodiments provide continuous monitoring, where the device monitors for laryngeal vibration and titrates up if detection is lost. The titration is initiated only by a triggering event, such as a detected cough, a loss in laryngeal vibration, and the like, rather than a daily titration or in addition to daily titration.

Various embodiments limit the neural stimulation system to an upper bound. In an embodiment, the intensity (e.g. amplitude) of the neural stimulation is increased only to a maximum value because of considerations such as safety, charge density limitations, longevity, and the like. For example, if the maximum value is reached before laryngeal vibration or cough is detected, the titration therapy would be limited to the maximum value.

Various embodiments limit the neural stimulation based on a clinician-supplied goal. For example, the physician may be provided with a programmable parameter for maximum amplitude. The physician may want to program a maximum allowed therapy intensity (e.g. stimulation amplitude) that is lower than the system limit. The patient may not initially be able to tolerate that value, but can as the patient accommodates to the therapy. The system continues to attempt up-titrating at some period frequency until the physician supplied goal is met.

Various embodiments provide an offset from a cough threshold. For example, the offset can be a safety margin of one or two or more steps down from the level that elicit a cough. This could be a nominal or a programmable value to allow physician choice.

Various embodiments provide an offset from a laryngeal vibration threshold. For example, a safety margin of one or two or more steps up (or down) from the level that elicited laryngeal vibration. This could be a nominal or a programmable valued to allow physician choice. If a conflict arises between laryngeal vibration threshold plus offset, and cough threshold less offset, then an embodiment sets the level to the greater of laryngeal vibration threshold plus offset or cough threshold less offset. Other resolutions for the conflict may be implemented.

Various embodiments delay a scheduled titration, such as a daily titration or a periodic titration, or a triggered titration. Titration may be delayed if the system detects that the patient is speaking. Titration during speaking may cause patient annoyance. Posture (patient standing), activity, heart rate, arrhythmia detection may be used to determine when to delay titration. Some embodiments provide a triggered titration down due to cough detection without delay, but allow titration triggered for other reasons to be delayed.

Figure 32:
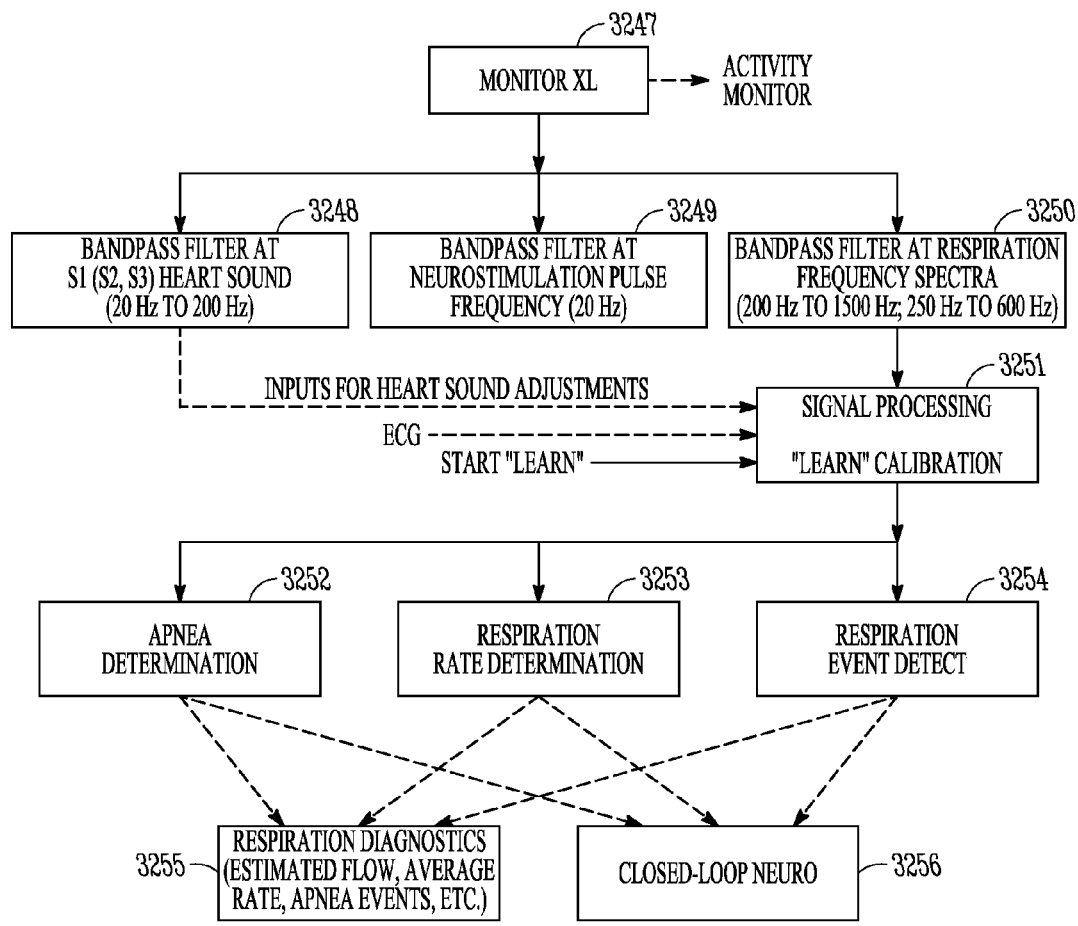
FIG. 32 illustrates an embodiment of a method for using an accelerometer to remotely sense respiratory parameter(s) for diagnostic purposes or for a closed loop neural stimulation.

FIG. 32 illustrates an embodiment of a method for using an accelerometer to remotely sense respiratory parameter(s) for diagnostic purposes or for a closed loop neural stimulation. At 3247, an accelerometer is monitored to provide an acoustic signal. This acoustic signal from the accelerometer may be filtered to provide an indicator of a heart sound as illustrated at 3248, to provide an indicator of neural stimulation as illustrated at 3249, and/or to provide an indicator of respiration as represented at 3250. At 3251, the signal indicative of respiration is processed. The heart sounds may be used in the signal processing to remove heart sound contributions from the signal. An ECG signal may also be used by a learning module to individualize the respiratory signal. The processed respiratory signal may be used to detect apnea as illustrated at 3252, to detect respiratory rate as illustrated at 3253, and to detect a respiratory event as illustrated at 3254. Apnea, respiration rate and/or respiration events may be used to provide respiration diagnostics 3255 or a closed loop neural stimulation therapy 3256. Examples of respiration diagnostics includes estimated flow, average rate, apnea events, and the like.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a sequence of instructions which, when executed by one or more processors, cause the processor(s) to perform the respective method. In various embodiments, the methods are implemented as a set of instructions contained on a computer-accessible medium such as a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system comprising:
    a neural stimulator having a housing with an electrode on the housing and having a neural stimulation lead with an electrode on the neural stimulation lead, the neural stimulator configured to deliver a neural stimulation therapy through the neural stimulation lead and remotely sense a heart rate using the electrode on the neural stimulation lead and the electrode on the housing of the neural stimulator.

2. The system of claim 1 wherein the neural stimulator is further configured to apply or withhold neural stimulation in response to the remotely sensed heart rate, or to trigger a therapy titration based on the remotely sensed heart rate.

3. The system of claim 1 wherein the neural stimulator is further configured to make a diagnostic prediction based on the remotely sensed heart rate.

4. The system of claim 1 wherein the neural stimulator is further configured to treat epilepsy or depression, or pain or obesity, or neuropsychiatric disorders.

5. The system of claim 2 wherein the neural stimulator is configured to trigger the therapy titration, including delivering the highest tolerable neural stimulation therapy without increasing the heart rate or an AV delay.

6. The system of claim 2 wherein the neural stimulator is configured to trigger the therapy titration, including delivering the highest tolerable neural stimulation therapy that increases the heart rate or an AV delay.

7. The system of claim 1 wherein the neural stimulator is further configured to sense an arrhythmia.

8. The system of claim 1 wherein the neural stimulator is further configured to sense a change in heart rate.

9. The system of claim 1, wherein the neural stimulator is further configured to monitor a cardiac activity including an average heart rate over periods of time during an implementation of a neural stimulation therapy.

10. The system of claim 1, wherein the neural stimulator is further configured to monitor a cardiac activity including a trending heart rate.

11. A method comprising:
    providing a neural stimulator having a housing with an electrode on the housing and having a neural stimulation lead with an electrode on the neural stimulation lead;
    delivering a neural stimulation therapy through the neural stimulation lead;
    remotely sensing a heart rate using the electrode on the neural stimulation lead and the electrode on the housing of the neural stimulator.

12. The method of claim 11 further comprising applying or withholding neural stimulation in response to the remotely sensed heart rate, or triggering a therapy titration based on the remotely sensed heart rate.

13. The method of claim 11 further comprising making a diagnostic prediction based on the remotely sensed heart rate.

14. The method of claim 11 further comprising treating epilepsy.

15. The method of claim 2 further comprising delivering the highest tolerable neural stimulation therapy without increasing the heart rate or an AV delay.

16. The method of claim 2 further comprising delivering the highest tolerable neural stimulation therapy that increases the heart rate or an AV delay.

17. The method of claim 11 further comprising sensing an arrhythmia.

18. The method of claim 11 further comprising monitoring a cardiac activity including an average heart rate over periods of time during an implementation of a neural stimulation therapy.

19. The method of claim 11 further comprising monitoring a cardiac activity including a trending heart rate.

20. A system comprising:
- means for providing a neural stimulator having a housing with an electrode on the housing and having a neural stimulation lead with an electrode on the neural stimulation lead;
- means for delivering a neural stimulation therapy through the neural stimulation lead;
- means for remotely sensing a heart rate using the electrode on the neural stimulation lead and the electrode on the housing of the neural stimulator.

* * * * *